(12) United States Patent
Hennessey et al.

(10) Patent No.: US 7,807,419 B2
(45) Date of Patent: Oct. 5, 2010

(54) PROCESS FOR CONCENTRATED BIOMASS SACCHARIFICATION

(75) Inventors: Susan M. Hennessey, Avondale, PA (US); Mayis Seapan, Landenberg, PA (US); Richard T. Elander, Evergreen, CO (US); Melvin P. Tucker, Lakewood, CO (US)

(73) Assignees: E. I. du Pont de Nemours and Company, Wilmington, DE (US); Alliance for Sustainable Energy LLC, Golden, CO (US)

( * ) Notice: Subject to any disclaimer, the term of this patent is extended or adjusted under 35 U.S.C. 154(b) by 551 days.

(21) Appl. No.: 11/843,114

(22) Filed: Aug. 22, 2007

(65) Prior Publication Data

US 2009/0053777 A1 Feb. 26, 2009

(51) Int. Cl.
C12P 19/00 (2006.01)
C12P 19/02 (2006.01)
C12P 19/04 (2006.01)
C12P 19/06 (2006.01)
C12P 7/18 (2006.01)

(52) U.S. Cl. .................. 435/101; 435/72; 435/105; 435/158; 435/160; 435/161

(58) Field of Classification Search .................. None
See application file for complete search history.

(56) References Cited

U.S. PATENT DOCUMENTS

| | | | |
|---|---|---|---|
| 4,409,329 A | 10/1983 | Silver | |
| 5,008,473 A | 4/1991 | Breitkopf et al. | |
| 5,192,673 A | 3/1993 | Jain et al. | |
| 5,356,812 A | 10/1994 | Matsuyama et al. | |
| 5,498,766 A | 3/1996 | Stuart et al. | |
| 6,013,494 A | 1/2000 | Nakamura et al. | |
| 6,159,738 A | 12/2000 | Donnelly et al. | |
| 6,228,630 B1 | 5/2001 | Kofod et al. | |
| 6,358,717 B1 | 3/2002 | Blaschek et al. | |
| 6,514,733 B1 | 2/2003 | Emptage et al. | |
| 6,777,207 B2 | 8/2004 | Kjeldsen et al. | |
| 6,861,237 B2 | 3/2005 | Anderson et al. | |
| 6,962,805 B2 | 11/2005 | Asakura et al. | |
| 7,598,069 B2 * | 10/2009 | Felby et al. ........... | 435/209 |
| 2003/0162271 A1 | 8/2003 | Zhang et al. | |
| 2003/0170834 A1 | 9/2003 | Gatenby et al. | |
| 2005/0250192 A1 | 11/2005 | Shanmugam et al. | |
| 2006/0003429 A1 | 1/2006 | Frost et al. | |
| 2007/0029252 A1 | 2/2007 | Dunson et al. | |
| 2007/0031918 A1 | 2/2007 | Dunson, Jr. et al. | |

FOREIGN PATENT DOCUMENTS

| | | |
|---|---|---|
| DE | 3150750 | 6/1983 |
| EP | 0 136 359 A1 | 4/1985 |
| EP | 0 263 515 A2 | 4/1988 |
| EP | 332234 B1 | 9/1989 |
| JP | 47004505 | 3/1972 |
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| WO | 2006/056838 | 6/2006 |
| WO | WO 2007/041269 A2 | 4/2007 |
| WO | WO 2007/050671 A2 | 5/2007 |

OTHER PUBLICATIONS

Jorgensen et al., Biotechnology and Bioengineering, vol. 96, No. 5, Apr. 1, 2007, pp. 862-870.
Mais et al., Applied Biochemistry and Biotechnology, vols. 98-100, pp. 815-832, 2002.
Li et al., Ultrasonics Sonochemistry, 12 (2005), pp. 373-384.
International Search Report of related PCT/US2008/073415 mailed Jul. 6, 2009.
U.S. Appl. No. 11/741,892, filed Apr. 30, 2007, Gail K. Donaldson et al.
U.S. Appl. No. 11/741,916, filed Apr. 30, 2007, Gail K. Donaldson et al.
U.S. Appl. No. 60/847,813, filed Sep. 28, 2006, Paul V. Vitanen et al.
U.S. Appl. No. 60/847,856, filed Sep. 28, 2006, Paul V. Vitanen et al.
U.S. Appl. No. 11/403,087, filed Apr. 12, 2006, James B. Dunson, Jr., et al.
Lynd et al., Microbial Cellulose Utilization: Fundamentals and Biotechnology, Microbiol. Mol. Biol. Rev., 2002, vol. 66:506-577.
N. Harnby et al., Mixing in the Process Industries, $2^{ND}$ Edition, 1997, p. 20.
Eur. J. Biochem., Nomenclature of the International Union of Biochemistry and Molecular Biology, Supplement: Corrections and Additions, 1994, vol. 223:1-5.
Eur. J. Biochem., Nomenclature Committee of the International Union of Biochemistry and Molecular Biology, Supplement 2: Corrections and Additions, 1995, vol. 232:1-6.
Eur. J. Biochem., Nomenclature Committee of the International Union of Biochemistry and Molecular Biology, Supplement 3: Corrections and Additions, 1996, vol. 237:1-5.
Eur. J. Biochem., Nomeclature Committee of the International Union of Biochemistry and Molecular Biology, Supplement 4: Corrections and Additions, 1997, vol. 250:1-6.

(Continued)

Primary Examiner—Herbert J. Lilling

(57) ABSTRACT

Processes for saccharification of pretreated biomass to obtain high concentrations of fermentable sugars are provided. Specifically, a process was developed that uses a fed batch approach with particle size reduction to provide a high dry weight of biomass content enzymatic saccharification reaction, which produces a high sugars concentration hydrolysate, using a low cost reactor system.

24 Claims, 4 Drawing Sheets

OTHER PUBLICATIONS

Eur. J. Biochem., Nomenclature Committee of the International Union of Biochemistry and Molecular Biology, Enzyme Supplement 5, 1999, vol. 264:610-650.
Jones et al., Acetone-Butanol Fermentation Revisted, Microbiological Reviews, 1986, vol. 50:484-524.
Underwood et al., Genetic Changes to Optimize Carbon Partitioning Between Ethanol and Biosynthesis in Ethanologenic *Escherichia Coli*, Appl. Environ. Microbiol., 2002, vol. 68:6263-6272.
Zhou et al., Production of Optically Pure D-Lactic Acid in Mineral Salts Medium by Metabolically Engineered *Escherichia Coli* W3110, Appl. Environ. Micorbiol., 2003, vol. 69:399-407.
Tay et al., Production of L(+) Lactic Acid From Glucose and Starch by Immobilized Cells of Rhizopus Oryzae in Rotating Fibrous Bed Bioreactor, Biotechnol. Bioeng., 2002, vol. 80:1-12.
Niu et al., Benzene-Free Synthesis of Adipic Acid, Biotechnol. Prog., 2002, vol. 18:201-211.
Cheryan et al., Production of Acetic Acid by Clostridium Thermoaceticum, Adv. Appl. Microbiol., 1997, vol. 43:1-33.
Freer, Acetic Acid Production by Dekkera/Brettanomyces Yeasts, World J. Microbiol. Biotechnol., 2002, vol. 18:271-275.
Lin et al., Metabolic Engineering of Aerobic Succinate Production Systems in *Escherichia Coli* to Improve Process Productivity and Achieve the Maximum Theoretical Succinate Yield, Metab. Eng., 2005, vol. 7:116-127.
Li et al., Efficient Pyruvate Production by a Multi-Vitamin Auxotroph of Torulopsis Glabrata? Key Role and Optimization of Vitamin Levels, Appl. Microbiol. Technol., 2001, vol. 55:680-685.
Yokota et al., Pyruvic Acid Production by an F-ATPASE Mutant of *Escherichia Coli* W1485LIP2, Biosci. Biotech. Biochem., 1994, vol. 58:2164-2167.
Suwannakham et al., Enhanced Propionic Acid Fermentation by Propionibacterium Acidipropionici Mutant Obtained by Adaptation in a Fibrous-Bed Bioreactor, Biotechnol. Bioeng., 2005, vol. 91:325-337.
Wu et al., Extractive Fermentation for Butyric Acid Production From Glucose by Clostridium Tyobutyricum, Biotechnol. Bioeng., 2003, vol. 82:93-102.
Janssen, Propanol as an End Product of Threonine Fermentation, Arch. Microbiol., 2004, vol. 182:482-486.
Anantassiadis et al., Prcoess Optimization of Continuous Gluconic Acid Fermentation by Isolated Yeast-Like Strains of Aureobasidium Pullulans, Biotechnol. Bioeng., 2005, vol. 91:494-501.
Singh et al., Optimisation of Fermentation Conditions for Gluconic Acid Production by a Mutant of Aspergillus Niger, Indian J. Exp. Biol., 2001, vol. 39:1136-1143.
Elfari et al., A Gluconobacter Oxydans Mutant Converting Glucose Almost Quantitatively to 5-KETO-D-Gluconic Acid, Appl. Microbiol. Biotech., 2005, vol. 66:668-674.
Reddy et al., Enhanced Production of Itaconic Acid From Corn Starch and Market Refuse Fruits by Genetically Manipulated Aspergillus Terreus SKR10, Bioresour. Technol., 2002, vol. 85:69-71.
Ui-Haq et al., Optimization of Nitrogen for Enhanced Citric Acid Productivity by a 2-Deoxy D-Glucose Resistant Culture of Aspergillus Niger NG-280, Bioresour. Technol., 2005, vol. 96:645-648.
Mussatto et al., Xylitol Production From High Xylose Concentration: Evaluation of the Fermentation in Bioreactor Under Different Stirring Rates, J. Appl. Microbiol., 2003, vol. 95:331-337.
Gorenflo et al., Development of a Process for the Biotechnological Large-Scale Production of 4-Hydroxyvalerate-Containing Polyesters and Characterization of Their Physical and Mechanical Properties, Biomacromolecules, 2001, vol. 2:45-57.
Ui et al., Production of L-2,3 Butanediol by a New Pathway Constructed in *Escherichia Coli*, Lett. Appl. Microbiol., 2004, vol. 39:533-537.
Okamoto et al., Development of an Industrially Stable Process for L-Threonine Fermentation by an L-Methionine-Auxotrophic Mutant of *Escherichia Coli*, J. Biosci. Bioeng., 2000, vol. 89:79-87.
Kumar et al., Effect of Cysteine on Methionine Production by a Regulatory Mutant of Corynebacterium Lilium, Bioresour. Technol., 2005, vol. 96:287-294.
Durre, Appl. New Insights and Novel Developments in Clostridial Acetone/Butanol/Isopropanol Fermentation, Microbiol. Biotechnol., 1998, vol. 49:639-648.
Groot et al., Technologies for Butanol Recovery Intergrated With Fermentations, Process. Biochem., 1992, vol. 27:61-75.
Bird et al., The Rheology and Flow of Viscoplastic Materials, Reviews in Chemical Engineering, 1983, vol. 1:1-70.
Yamadaya et al., Hydrocracking of Tetralin on Supported Nickel-Tungsten Catalysts, Bullentin of the Chemical Society of Japan, 1977, vol. 50:79-87.
Nakayama et al., Fermentative Production of L-Arginine, Arg. Biol. Chem., 1972, vol. 36:1675-1684.

* cited by examiner

PROCESS FOR CONCENTRATED BIOMASS SACCHARIFICATION

STATEMENT OF GOVERNMENT RIGHTS

This invention was made with United States Government support under Contract Nos. 04-03-CA-70224 and DE-FC36-03GO13146 awarded by the Department of Energy. The government has certain rights in this invention.

FIELD OF THE INVENTION

Processes for saccharification of pretreated biomass to obtain high concentrations of fermentable sugars are provided. Specifically, a process was developed that uses a fed batch approach with particle size reduction to provide a high dry weight of biomass content enzymatic saccharification reaction, which produces a high sugars concentration hydrolysate, using a low cost reactor system.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily amenable to saccharification enzymes. The pretreatment mixture is then further hydrolyzed in the presence of a saccharification enzyme consortium to release oligosaccharides and/or monosaccharides in a hydrolysate. Saccharification enzymes used to produce fermentable sugars from pretreated biomass typically include one or more glycosidases, such as cellulose-hydrolyzing glycosidases, hemicellulose-hydrolyzing glycosidases, and starch-hydrolyzing glycosidases, as well as peptidases, lipases, ligninases and/or feruloyl esterases. Saccharification enzymes and methods for biomass treatment are reviewed in Lynd, L. R., et al. (Microbiol. Mol. Biol. Rev. (2002) 66:506-577).

In order for the saccharification product, the biomass hydrolysate, to be used in subsequent fermentation production in an economical manner, it should contain a high concentration of sugars. A sugar concentration that is above 14% is desired in hydrolysate used for fermentation to ethanol, to produce ethanol at an economically viable level. For most types of lignocellulosic biomass, this corresponds to using a biomass dry matter content above 20% in a saccharification process. High sugar yielding saccharification of biomass at this high biomass concentration in an economically feasible reactor system has been heretofore been difficult to achieve.

Thus, there remains a need for an economical process for saccharification of biomass which can be carried out using a high dry weight of biomass such that the yields are high and the resulting hydrolysate contains a high concentration of fermentable sugars. In order to accomplish said economies and results, the process must provide for sufficient temperature and pH control. Applicants have been able to develop such a process by manipulating the biomass in ways that sustain thorough mixing in a low cost traditional stirred tank reactor system.

SUMMARY OF THE INVENTION

The present invention provides a process for saccharifying pretreated biomass at a high dry weight biomass to produce fermentable sugars. The process of the invention uses a fed batch reactor system including multiple size reduction steps and mixing to maintain thorough mixing in a vertical, agitated tank. In one embodiment of the invention, the process comprises:

a) providing a portion of reaction components in a vertical stirred tank reactor having a particle size reduction mechanism, said reaction components comprising:
  i) a portion of a mixable pretreated biomass slurry; and
  ii) a portion of a first saccharification enzyme consortium comprising at least one enzyme capable of hydrolyzing cellulose;
b) reacting said slurry and enzymes under suitable conditions;
c) applying the particle size reduction mechanism;
d) adding an additional portion of pretreated biomass producing a higher solids biomass slurry;
e) optionally adding an additional portion of a saccharification enzyme consortium;
f) reacting said higher solids biomass slurry under suitable conditions; and
g) optionally repeating one or more steps (c), (d), (e), and (f) one or more times, whereby a high sugar content hydrolysate is produced and wherein the yield stress of the slurry is maintained at less than 30 Pa.

Additional aspects of the present invention are directed to the hydrolysate that has been prepared using the present process and a target chemical produced by fermentation of the hydrolysate that has been prepared using the present process.

DETAILED DESCRIPTION OF THE INVENTION

Figure 1:
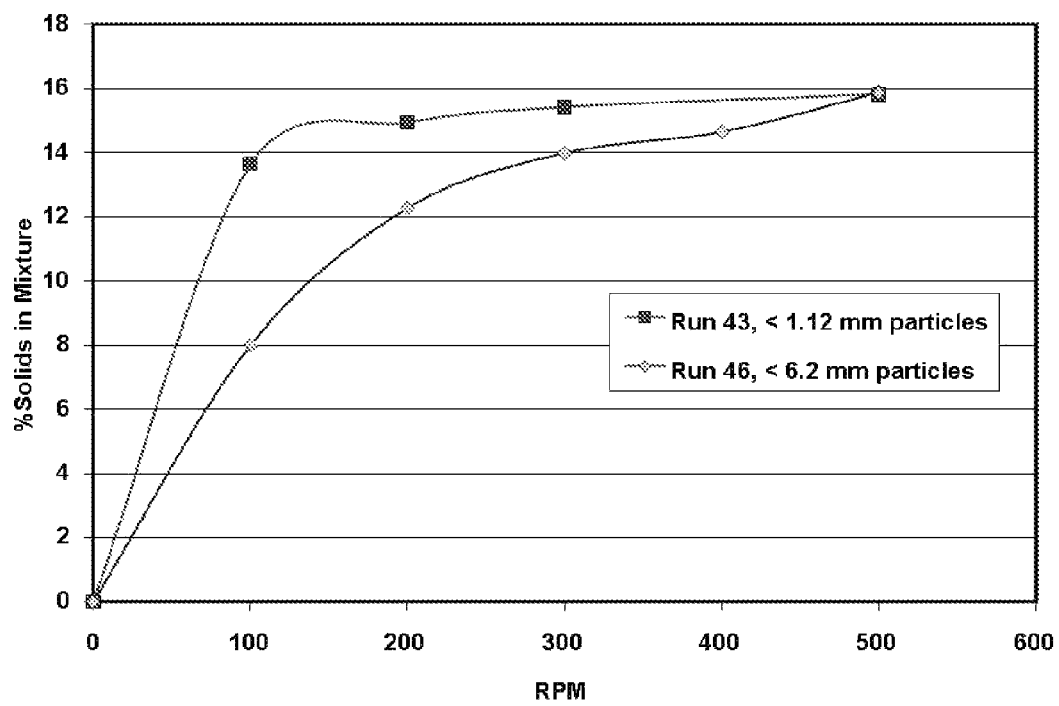
FIG. 1 shows a graph of the stagnation limits of corn cob biomass in a saccharifier.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for saccharifying a high dry weight of biomass that produces a high concentration of fermentable sugars in the resulting hydrolysate. In the present process, the biomass is introduced into a reactor using a fed batch system, the biomass undergoes multiple size reduction steps, and the reactor contents are well mixed allowing good pH and temperature control during saccharification using saccharification enzymes. The process is amenable to mixing in a vertical reactor with overhead agitation, which that can be scaled up to very large volumes economically. The size reduction steps that are included in the saccharification process promote an increased rate of reaction of cellulose and/or hemicellulose with saccharifying enzymes, allowing for rapid liquefaction of the pretreated wet solid biomass and use of this low cost rector. Combined size reduction, faster enzymatic saccharification and the fed batch process of biomass loading, prevent the reactor contents from developing a significant yield stress, thus allowing complete mixing in a vertical tank reactor (including impellers and motor). Complete mixing and prevention of stagnation, provides for better pH and temperature control. With such control, hydrolysates with high dry weight biomass may be made with high yields of sugars. The resulting high concentration sugar hydrolysate may be used in fermentations to produce valuable products such as fuels and other chemicals, including ethanol.

Definitions

In this disclosure, a number of terms are used. The following definitions are provided:

The term "Biomass" refers to any cellulosic or lignocellulosic material and includes materials comprising cellulose, and optionally further comprising hemicellulose, lignin, starch, polysaccharides, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure. In one embodiment, biomass that is useful for the invention includes biomass that has a relatively high carbohydrate value, is relatively dense, and/or is relatively easy to collect, transport, store and/or handle. In one embodiment of the invention, biomass that is useful includes corn cobs, corn stover and sugar cane bagasse.

The term "pretreated biomass" means biomass that has been subjected to a treatment or pretreatment prior to saccharification. Treatments such as pretreatments are further described herein.

The term "lignocellulosic" refers to a composition comprising both lignin and cellulose. Lignocellulosic material may also comprise hemicellulose.

The term "cellulosic" refers to a composition comprising cellulose.

The term "saccharification" refers to the production of fermentable sugars from polysaccharides.

The term "fermentable sugar" refers to oligosaccharides and monosaccharides that can be used as a carbon source by a microorganism in a fermentation process.

The term "hydrolysate" refers to the product of saccharification, which contains the sugars produced in the saccharification process, the remaining un-hydrolyzed biomass, and the enzymes used for saccharification.

The term "slurry" refers to a mixture of insoluble material and a liquid.

The term "mixable slurry" refers to a slurry that becomes substantially homogeneous under the action of the agitation system to which it is subjected. "Mixability" refers to this property of a slurry.

The term "thoroughly mixed slurry" refers to a state where the components of the slurry are substantially evenly distributed (homogeneous) throughout the slurry.

The term "heel" refers to the initial liquid or slurry charged into a reactor before biomass is introduced and saccharification is started.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

The term "dry weight of biomass concentration" refers to the total amount of biomass dry weight added into a fed batch system reactor, calculated at the time of addition, as a percent of the total weight of the reacting composition in the reactor at the end of the run.

The term "suitable reaction conditions" refers to the time, temperature, ph and reactant concentrations which are described in detail below. Reaction conditions includes the mixing or stirring by the action of an agitator system in the vertical tank reactor, including but not limited to impellers. The mixing or stirring may be continuous or non-continuous, with, for example, interruptions resulting from adding additional components or for temperature and pH assessment.

In the present process, any pretreated biomass may be used. Biomass may be pretreated by any method known to one skilled in the art such as with acid, base, organosolvent, oxidizing agent, or other chemicals. Also, biomass may be pretreated with one or more chemicals in combination with steam, or with steam alone. Pretreatment may also include mechanical disruption such as by crushing, grinding, or chopping as well as application of other disrupting physical energies such as ultrasound or microwaves. In addition, non-pretreated biomass may be used, but more suitable is the use of biomass that has been pretreated to enhance subsequent saccharification. Biomass may initially be in a high dry weight concentration or in more dilute form such as is the case for stillage.

Applicants have developed a saccharification process for biomass that combines multiple size reductions and multiple biomass additions in a standard agitated vertical tank system that surprisingly keeps viscosity low enough to allow loading of the reactor with greater than 20% dry weight of biomass, while maintaining thorough mixing to provide efficient pH and temperature control. This process results in high yields of sugars. In one embodiment, a dry weight of biomass concentration of about 38% was achieved. Thus an economical biomass saccharification process has been achieved.

Biomass is introduced into a vertical reactor tank equipped with an overhead agitator system such as a motor and shaft with one or more impellers. The number and types of impellers used on the shaft are designed to provide adequate flow and solids suspension within the reactor at the various stages of saccharification. Preferred impellers are high flow designs which have low power numbers and hence low power requirements, thus decreasing the motor size required in the low cost reactor system. High flow impellers with low power numbers that may be used are well known to one skilled in the art, and may include, for example, pitched-blade turbines or hydrofoils. High flow impellers are commercially available, for example: Lightnin A310 (Cole-Parmer, Vernon Hills, Ill.), APV LE hydrofoil (Invensys APV, Getzville, N.Y.), and Chemineer HE-3 (Chemineer, Inc., Dayton, Ohio).

In other high solids saccharification systems, such as a horizontal tank rotating system, initial power requirements to mix the starting wet solid biomass are high and then dissipate as the wet solid liquefies. Other disadvantages with horizontal mixing systems are the large agitator with low clearance to the wall and the submerged agitator seal, which tends to leak and be a maintenance issue.

In the present process, biomass is present in the reactor, from the beginning of the saccharification process, in the form of a mixable slurry. A mixture of insoluble material and a liquid is a mixable slurry when it becomes substantially homogeneous under the action of the agitation system to which it is subjected. The present process maintains the yield stress of the biomass mixable slurry throughout saccharification at less than about 30 Pa. The yield stress is a measure of the minimum stress that is required to break down the structure sufficiently before any movement will occur (Mixing in the Process Industries, $2^{nd}$ Edition, N. Harnby et. al. p 20 (1997)). In biomass slurries with a higher yield stress, the yield stress may be overcome by adding extra impellers and running them at higher speed thus requiring a larger motor. As the yield stress of the fluid increases, the agitator system needed to obtain mixability becomes uneconomical. Thus by maintaining the yield stress of the biomass mixable slurry at less than about 30 Pa, the agitator system required for mixing is an economical one in terms of structure and power requirements.

In the present process, pretreated biomass loaded into the reactor may be already in the form of a mixable slurry, or if it has a solids content that makes it not mixable, then liquid is included to the point of making it a mixable slurry. Biomass that may be in an initial form as a mixable slurry may include, for example, stillage or biomass pretreated in a process that uses a high liquid component. For biomass that is not in mixable slurry form, liquid may be added prior to loading, or the biomass may be loaded into a reactor that is preloaded with a liquid. The liquid may be water, fresh or recycled from other parts of the process, thin stillage from a corn dry grind operation, a portion of hydrolysate left behind from a previous batch, as is or diluted, or various other high water streams. For example, an initial heel of liquid is charged into the reactor and then biomass is introduced to form a biomass slurry that sustains thorough mixing under action of the vertical agitator. The slurry may be brought to as high of a dry weight of biomass content that may be included while not exhibiting a yield stress that the vertical agitator system can not overcome to maintain mixability, and not exceeding about 30 Pa. The exact weight will vary depending on the type of biomass, size of reactor and stirring mechanism, and can be readily determined by one skilled in the art. Mixability may be assessed by any applicable method such as visual inspection, using a probe such as a laser optical probe to assess movement of particles, or by sampling and assaying for homogeneity or viscosity. The biomass in this initial loading is a portion of the total biomass used in a saccharification run. Additional portions of biomass are added during saccharification as described below.

A portion may be less than 5, 10, 20, 30, 40, 50, 60, 70, 80, 90 or 100% of the biomass or other reaction components added at any one step.

While mixing, the slurry is brought to a desired pH through addition of acid or base as required, depending on the initial pH of the biomass, which will vary depending on the pretreatment used. The specific pH that is desired is based upon the pH optima for the saccharification enzymes to be used with the particular type of biomass being processed, as described below. Thorough mixing of the biomass slurry ensures that a substantially uniform pH is achieved throughout the biomass material, allowing optimal functioning of the saccharification enzymes. The importance of maintaining the desired pH is demonstrated in Example 5 herein, where it is shown that a shift in pH from the target reduces the sugars yield.

While mixing, the slurry is also brought to the desired temperature by either heating or cooling of the biomass slurry. The specific temperature that is desired is based upon the temperature optima for the saccharification enzymes to be used with the particular type of biomass being processed, as described below, to achieve the best possible saccharification reaction rate. One may also choose to operate at a lower temperature, for other processing reasons, without detrimental effect to the enzymes, although enzyme activity may be decreased at lower than optimal temperature. Saccharification enzymes are added to the biomass slurry following pH and temperature adjustment. This is a portion of saccharification enzymes that is added to the initial mixable pretreated biomass. Additional saccharification enzymes may be added following addition of more biomass portions in the fed batch process described below, or could all be added at the beginning. Furthermore, various enzymes may be added at different times to achieve optimum saccharification efficiency.

Saccharification enzymes, which also may be referred to as a saccharification enzyme consortium, are used to hydrolyze the biomass releasing oligosaccharides and/or monosaccharides in a hydrolysate. Saccharification enzymes are reviewed in Lynd, L. R., et al. (Microbiol. Mol. Biol. Rev. (2002) 66:506-577). A saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases, called hemicellulases, (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzymes used in the present method comprise at least one "cellulase", and this activity may be catalyzed by more than one enzyme. Optionally, the saccharification enzymes used in the present method may comprise at least one hemicellulase, generally depending on the type of pretreated biomass used in the present process. For example, hemicellulase is typically not needed when saccharifying biomass pretreated with acid and is typically included when saccharifying biomass pretreated under neutral or basic conditions.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms. New saccharification enzymes may be developed, which may be used in the present process.

One skilled in the art will know how to determine the effective amounts of enzymes to use in the present process and how to adjust conditions for optimal enzyme activity. One skilled in the art will also know how to optimize the classes of enzyme activities required to obtain optimal saccharification of a given pretreatment product under the selected conditions. Preferably, saccharification is performed at or near the pH and temperature optima for the saccharification enzymes being used. The pH optimum can range from about 4 to about 10, and is more typically between about 4.5 and about 6. The temperature optimum can range between about 20° C. to about 80° C., and is more typically between about 25° C. and about 60° C.

As saccharification proceeds, soluble sugars are produced from the cellulose and/or hemicellulose in the biomass, thereby liquefying non-soluble components of the biomass slurry. The biomass in the slurry becomes partially hydrolyzed. The slurry becomes less viscous, allowing additional biomass to be added to the slurry while maintaining the mixability of the slurry with the vertical agitator in the reactor. Additional biomass may be added to the slurry in an amount less than that which would increase the yield stress of the slurry to >30 Pa, to allow thorough mixing with an economical vertical agitator system. The additional portion of biomass adds more solids and thus increases the percent of total solids loaded in the saccharifying slurry. As additional biomass is added, the pH and temperature are controlled within the preferred ranges while mixing and the saccharification reaction continues. The thorough mixing of the slurry allows control of pH in a narrow range as more biomass is added and acid or base is added to make pH adjustments. The tight pH control allowed in the present process enhances saccharification by improving saccharification enzyme function. The thorough mixing of the slurry allows control of the temperature of the reactor contents in a narrow range as more biomass is added, which also improves saccharification enzyme function. Sources of heat or cooling that may be used are well known to one skilled in the art, and may include a jacket on the reactor, internal coils in the reactor, or a heat exchanger through which the reactor contents is pumped. The tight temperature control allowed in the present process enhances saccharification by allowing the saccharification to run at the highest temperature possible without overshooting the reactor temperature and thermally inactivating the enzymes.

Additional portions of a saccharification enzyme consortium may optionally be added following one or more new biomass loadings. Each added portion of a saccharification enzyme consortium may include the same enzymes as in the initially added saccharification enzyme consortium, or it may include a different enzyme mixture. For example, the first added saccharification enzyme consortium may include only or primarily cellulases, while a later added saccharification enzyme consortium may include only or primarily hemicellulases. Any saccharification enzyme consortium loading regime may be used, as determined to be best at saccharifying the specific biomass in the reactor. One skilled in the art can readily determine a useful saccharification enzyme consortium loading regime, such as is described in Example 10 herein.

Liquefaction of biomass results from further saccharification, thereby again reducing biomass slurry viscosity and yield stress, if present, and allowing addition of more biomass while retaining mixability. Thus additional biomass may be added following a fed batch system, while maintaining stirring by the vertical agitator. The additional biomass feedings may be semi-continuous, allowing periods of liquefaction between additions. Alternatively, the biomass feeding may be continuous, at a rate that is slow enough to balance the continuous liquefaction occurring during saccharification. In either case, mixability of the slurry is monitored and biomass addition is controlled to maintain thorough mixing as determined by the agitator system overcoming the yield stress of the slurry.

In the present process, the particle size of the non-soluble biomass is also repeatedly reduced. Reduction of particle size was shown herein to significantly decrease reaction time and increase yield. Some reduction in particle size occurs during the stirring and saccharification as described herein in Examples 2 and 3. Particle size reduction is enhanced in the present process by multiple applications of mechanical force for this purpose. A mechanical particle size reduction mechanism may be, for example, a blender, grinder, shearer, chopper, sheer disperser, disperser, or roto-stat. Particle size reduction may also be imposed by other non-mechanical methods, such as ultrasonic methods. The particle size may be reduced prior to initial production of a slurry for saccharification, prior to addition of pretreated biomass to an existing saccharifying slurry, and/or during saccharification of a slurry. For example, a chopping blade or high-speed disperser may be immersed in the saccharifying slurry to reduce particle size. Also the size of the incoming pretreated biomass may be reduced by passing through a grinder or disk refiner. In one embodiment, a recycle loop with an incorporated in-line grinder is attached to the biomass reactor such that particles are reduced in size as slurry enters the loop, passes through the grinder, and then re-enters the reactor. In any of these cases, the mixability of the slurry may be monitored to optimize particle size reduction for maximal incorporation of dry weight of biomass and maximal production of sugars in the resulting hydrolysate.

The recycle loop with in-line grinder may also incorporate a temperature control point, such as by including an in-line heat exchanger. Controlling the temperature of the biomass slurry re-entering the reactor from the recycle loop provides temperature control of the saccharifying slurry by the thorough mixing of the vertical agitator. In the same manner, controlling the temperature of the biomass added in the fed batch system provides a means of temperature control of the saccharifying slurry. The temperature is controlled to provide a temperature necessary for optimal activity of the saccharifying enzymes, as noted previously.

In the present process using a fed batch system, biomass is added until a dry weight of biomass loading of at least above 20% is achieved. The percent dry weight of biomass loading is given as the amount of dry weight of biomass added into the reactor relative to the total weight of the reacted composition, or hydrolysate, in the reactor at the end of the run. A fed batch run may last for about 12 hours to about 7 days. A 72 hour run is particularly suitable. In one embodiment biomass additions occur periodically during the first 12 to 24 hours. Biomass is added at least two times in the present process. In one embodiment biomass is added more than three times to reach a dry weight of biomass loading of 24%, or 30% in another embodiment. Biomass may be added to just below the point where the saccharifying slurry would have a yield stress above about 30 Pa, such that the agitator system could not overcome and achieve mixability.

Applicants have surprisingly found that through combining multiple size reductions and multiple biomass additions using the present process, saccharification of a dry weight of biomass concentration of greater than 20% may be achieved while maintaining a mixable slurry in a vertical agitator tank system. A dry weight of biomass concentration of about 24% or greater, or even 30% or greater, may be achieved. In one embodiment, a dry weight of biomass concentration of about 38% was achieved. Due to the high liquefaction of reduced particle size biomass in the present process, the high biomass solids content is reached while continuing to maintain a yield stress of less than 30 Pa that allows thorough mixing using the vertical agitation reactor. Applicants have surprisingly found that high sugar yields are attained with saccharification at these high biomass solids using this process that includes stirring, size reduction, maintenance of pH and temperature, and including additional biomass over time.

Using the vertical agitator tank system with size reduction requires much less energy than a horizontal rotating system and its capital cost is significantly less, thereby allowing production of sugars from high dry weight of biomass to be done in an economical reactor system while producing high yields of soluble sugars, comparable to yields using a lower percent solids saccharification. The high yield of soluble sugars has not been shown in the horizontal reactor system. Producing sugars from the high dry weight of biomass allows production of a hydrolysate containing a high concentration of sugars. The concentration of sugars in the hydrolysate produced in the present process is at least about 100 g/L of total soluble sugars, even higher than the 80 g/L that is typically considered to be high concentration sugars. Concentrations of sugars of 150 g/L, or of 200 g/L, and even higher, such as 240 g/L may be obtained. Glucose yields are greater than about 80%, while up to 90%, and even 95% or greater may be achieved. Glucose concentration in the hydrolysate is at least about 90 g/L, while concentrations of 100 g/L or better, such as about 140 g/L, may be achieved. Together the high sugars concentration hydrolysate product and the low capital cost production system requiring low energy input make the present process one that can be economically used as part of a process for making valuable fuels and other chemicals.

Alternatively to providing a fully saccharified hydrolysate product, the saccharification may be run until the final percent solids target is met and then the saccharifying biomass may be transferred to a fermentation process, where saccharification continues along with fermentation (called SSF: simultaneous saccharification and fermentation.)

Fermentable sugars produced in the present process may be fermented by suitable microorganisms that either naturally or through genetic manipulation are able to produce substantial quantities of desired target chemicals. Target chemicals that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids may include acetic acid, lactic acid, propionic acid, 3-hydroxypropionic acid, butyric acid, gluconic acid, itaconic acid, citric acid, succinic acid and levulinic acid. Amino acids may include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and may include *Escherichia, Zymomonas, Saccharomyces, Candida, Pichia, Streptomyces, Bacillus, Lactobacillus*, and Clostridiuma. Typically, biocatalysts may be recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*

Many biocatalysts used in fermentation to produce target chemicals have been described and others may be discovered, produced through mutation, or engineered through recombinant means. Any biocatalyst that uses fermentable sugars produced in the present method may be used to make the target chemical(s) that it is known to produce by fermentation.

Particularly of interest are biocatalysts that produce biofuels including ethanol and butanol. For example, fermentation of carbohydrates to acetone, butanol, and ethanol (ABE fermentation) by solventogenic *Clostridia* is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Co-owned and co-pending patent applications WO 2007/041269 and WO 2007/050671, which are herein incorporated by reference, disclose the production of 1-butanol and isobutanol, respectively, in genetically engineered microbial hosts. Co-owned and co-pending U.S. patent applications No. 11/741,892 and No. 11/741,916, which are herein incorporated by reference, disclose the production of 2-butanol in genetically engineered microbial hosts. Isobutanol, 1-butanol or 2-butanol may be produced from fermentation of hydrolysate produced using the present process by a microbial host following the disclosed methods.

Genetically modified strains of *E. coli* have also been used as biocatalysts for ethanol production (Underwood et al., (2002) Appl. Environ. Microbiol. 68:6263-6272). A genetically modified strain of *Zymomonas mobilis* that has improved production of ethanol is described in US 2003/0162271 A1. A further engineered ethanol-producing strain of *Zymomonas mobilis* and its use for ethanol production are described in co-owned and co-pending U.S. patent applications 60/847,813 and 60/847,856, respectively, which are herein incorporated by reference. Ethanol may be produced from fermentation of hydrolysate produced using the present process by *Zymomonas mobilis* following the disclosed methods. In Example 13 herein, the present process is used for saccharification of pretreated corn cob biomass to fermentable sugars, followed by fermentation of the sugars for the production of ethanol using *Z. mobilis* as the biocatalyst.

The present process may also be used in the production of 1,3-propanediol from biomass. Recombinant strains of *E. coli* have been used as biocatalysts in fermentation to produce 1,3 propanediol (U.S. Pat. No. 6,013,494, U.S. Pat. No. 6,514,733). Hydrolysate produced by saccharification using the present process may be fermented by *E. Coli* to produce 1,3-propanediol as described in Example 10 of co-owned and co-pending U.S. application Ser. No. 11/403,087, which is herein incorporated by reference.

Lactic acid has been produced in fermentations by recombinant strains of *E. Coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). Recombinant strains of *E. coli* have been used as biocatalysts in fermentation to produce 1,3 propanediol (U.S. Pat. No. 6,013,494, U.S. Pat. No. 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17cr1 (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-UI-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium*, *Brevibacterium*, and *Serratia*. For example, production of histidine using a strain resistant to a histidine analog is described in Japanese Patent Publication No. 56008596 and using a recombinant strain is described in EP 136359. Production of tryptophan using a strain resistant to a tryptophan analog is described in Japanese Patent Publication Nos. 47004505 and 51019037. Production of isoleucine using a strain resistant to an isoleucine analog is described in Japanese Patent Publication Nos. 47038995, 51006237, 54032070. Production of phenylalanine using a strain resistant to a phenylalanine analog is described in Japanese Patent Publication No. 56010035. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 54037235 and 57150381) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. No. 6,861,237, U.S. Pat. No. 6,777,207, U.S. Pat. No. 6,228,630).

Target chemicals produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

EXAMPLES

General Methods and Materials

The following abbreviations are used:

"HPLC" is High Performance Liquid Chromatography, "C" is Centigrade, "kPa" is kiloPascal, "m" is meter, "mm" is millimeter, "kW" is kilowatt, "µm" is micrometer, "µL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass, "ASME" is the American Society of Mechanical Engineers, "s.s." is stainless steel, in" or """ is inch, "PSD" is particle size distribution, "d-50" is the particle diameter where 50% of the cumulative volume of the particles is below this size, "d-95" refers to a particle diameter where 95% of the cumulative volume of the particles is below this size, "rpm" is revolutions per minute.

Sulfuric acid, ammonium hydroxide, acetic acid, acetamide, yeast extract, glucose, xylose, sorbitol, $MgSO_4.7H_2O$, phosphoric acid and citric acid were obtained from Sigma-Aldrich (St. Louis, Mo.).

Measurement of Cellulose and Hemicellulose in Biomass

The composition of biomass is measured by any one of the standard methods well known in the art, such as ASTM E1758-01 "Standard method for the determination of carbohydrates by HPLC".

Measurement of Sugars, Acetamide, Acetic Acid, and Lactic Acid Content

Soluble sugars (glucose, cellobiose, xylose, xylobiose, galactose, arabinose, and mannose) acetamide, acetic acid, and lactic acid in saccharification liquor were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with appropriate guard columns.

Monosaccharides were directly measured in the hydrolysate. The insoluble matter was removed from the hydrolysate by centrifuge. The pH of the separated liquid was adjusted, if necessary, to 5-6 for Bio-Rad HPX-87P column and to 1-3 for Bio-Rad HPX-87H column, with sulfuric acid. The separated liquid was diluted, if necessary, then filtered by passing through a 0.2 μm syringe filter directly into an HPLC vial.

For analysis of total dissolved sugars, 10 ml of diluted sample was placed in a pressure vial and 349 μl of 75% H2SO4 was added. The vial was capped and placed in the Autoclave for an hour to hydrolyze all sugars to monosaccharides. The samples were cooled and their pH was adjusted by sodium carbonate to the necessary pH, as described above, then the samples were filtered into the HPLC vials and analyzed by HPLC.

The HPLC run conditions were as follows:

Biorad Aminex HPX-87P (for carbohydrates):
Injection volume: 10-50 μL, dependent on concentration and detector limits
Mobile phase: HPLC grade water, 0.2 μm filtered and degassed
Flow rate: 0.6 mL/minute
Column temperature: 80-85° C., guard column temperature <60° C.
Detector temperature: as close to main column temperature as possible
Detector: refractive index
Run time: 35 minute data collection plus 15 minute post run (with possible adjustment for later eluting compounds)
Biorad Aminex HPX-87H (for carbohydrates, acetamide, acetic acid and lactic acid)
Injection volume: 5-10 μL, dependent on concentration and detector limits
Mobile phase: 0.01N Sulfuric acid, 0.2 μm filtered and degassed
Flow rate: 0.6 mL/minute
Column temperature: 55° C.
Detector temperature: as close to column temperature as possible
Detector: refractive index
Run time: 25-75 minute data collection After the run, concentrations in the sample were determined from standard curves for each of the compounds.

Measurement of Particle Size

The particle size distributions (PSD) of pretreated biomass and hydrolysate samples were measured using one or both of the techniques described below, depending on the size range of particles. For course particles that are larger than 2 mm, a wet sieving technique was used. The smaller particles were analyzed by a Beckman Coulter LS13320 instrument.

In wet sieving, the entire sample was washed through four selected sieves, stacked in order with the finest sieve at the bottom. The four sieves used in this work had openings of 2300, 2360, 2800, 3350 micrometers. Each sieve was then placed in a beaker containing just enough water to cover the wire mesh and dislodge the retained fine particles. The sieve was dipped and removed several times, allowing the finer particles to pass through the sieve into the liquid. The retained solids were then collected, dried, and weighed. The slurry, which passed though the single sieve, was poured onto the next sieve. This process was repeated for every selected sieve.

The Beckman Coulter LS13320 (Beckman Coulter, Inc., Miami, Fla.) is an instrument which uses laser diffraction technique to measure the PSD of materials using a wet module. The LS13320 can measure particles between 40 nanometers to 2000 micrometers. The samples were diluted by Millipore DI water and sonicated by ultrasonic probe for 10 minutes using a jacketed beaker, with cold water circulation to keep samples cool while sonicating them. The diluted slurry was introduced to the instrument recirculating system at 50% recirculation speed, until it reached optimum obscuration. After 30 minutes recirculation to allow complete mixing and equilibration, the PSD were measured. The measurements were repeated twice to verify the suspension stability and measurement reproducibility. The average of the two stable measurements was reported as the PSD of the sample.

The results are reported as d-50, which refers to a particle diameter where 50% of the cumulative volume of the particles is below this size. Similarly, d-95 refers to a particle diameter where 95% of the cumulative volume of the particles is below this size.

Measurement of Viscosity

The viscosity of hydrolysates was measured in a Starch Pasting Cell using a TA Instruments (New Castle, Del.) AR-G2 Rheometer. The rheology of the hydrolysates cannot be measured in regular concentric cylinder, cone and plate, or even vane and cylinder viscometers. The Starch Pasting Cell has a concentric cylinder geometry of a cup and bob. However, the bob is a special rotor that is designed to keep particles mixed and prevent sedimentation while measurement is taking place. The instrument is designed for temperature ramp at constant sheer rate. However, it can also be used for constant temperature measurement with increasing sheer, in a sheer range of 0.1 to 10 $s^{-1}$ with 10% accuracy. The data can be analyzed by Herschel-Bulkley model, (Bird, R. B., et al. Rev. Chem. Eng. (1983) 1:1-70), or can be plotted on a linear scale, as the sheer rate versus sheer stress. For fluids with no yield stress, this plot passes through the origin. However, for fluids with yield stress, the plot passes through a point where the sheer rate becomes zero, while the sheer stress has a positive value, which is considered as the yield stress.

Preparation of Pretreated Corn Cobs

The corn cobs used in these runs were prepared in one of the following reactors, as described in co-owned and co-pending US patent application # US20070031918A1.

Jaygo Reactor

The Jaygo reactor is a 130-liter (approximately 51 cm diameter×91 cm length), horizontal paddle type reactor (Jaygo Manufacturing, Inc., Mahwah, N.J.) fabricated of Hastelloy® C-22 alloy. The reactor is equipped with a steam jacket capable of heating to approximately 177° C. (862 kPa). Direct steam injection is also used to rapidly bring biomass up to pretreatment temperature. Steam pressure is adjusted and controlled to maintain the desired pretreatment temperature.

Steam Gun Reactor

The 4-liter steam explosion reactor (Autoclave Engineers, Erie, Pa.) is a steam-jacketed reactor consisting of a length of 102 mm schedule 80 Hastelloy® pipe closed by two ball valves. Additional electrical heaters are placed on all exposed, non-jacketed surfaces of the reactor and controlled to the pretreatment set point temperature. Direct steam injection is also used to rapidly bring biomass up to pretreatment temperature. Steam pressure is adjusted and controlled to maintain the desired pretreatment temperature. The bottom of the reactor is necked down to 51 mm. All pretreated material exits through a replaceable die at the bottom of the reactor and is collected in a nylon (Hotfill®) 0.21 m$^3$ bag supported within a heavy walled, jacketed, and cooled flash tank.

Pretreatment and Enzymatic Hydrolysis Reactor (PEHR)

This reactor is disclosed in co-owned and co-pending US Patent Application, Publication #US20070029252, which is herein incorporated by reference.

The 9-L PEHR (constructed at NREL, Golden, Colo.) has an approximately 15 cm×51 cm stainless steel reaction vessel with an injection lance for introduction of processing reactants. The injection lance is connected using a rotary joint to a port in a cover on one end of the vessel, which has an additional port for vessel access. Four baffles run the length of the vessel wall, and are attached perpendicularly to the wall. The baffles and twenty-two ceramic attrition media cylinders of 3.2 cm×3.2 cm (E.R. Advanced Ceramics, East Palestine, Ohio), free floating in the vessel, apply mechanical mixing of biomass and reactant as the vessel is rotated, promoting assimilation of reactant into the biomass. The PEHReactor is placed on a Bellco Cell-Production Roller Apparatus (Bellco Technology, Vineland, N.J.) which provides a mechanism for rotation, and the reactor with roller apparatus is housed in a temperature controlled chamber which provides heat. Vacuum and pressure may be applied to the reaction vessel by attaching external sources to the lance-connected port in the cover.

Large Barrel Piston Reactor

This reactor is disclosed in co-owned and co-pending US Patent Application CL3949, which is herein incorporated by reference.

The barrel piston reactor consisted of a 5.1 cm×68.6 cm stainless steel barrel equipped with a piston, oriented horizontally. The piston was sealed to the barrel with four O-rings and was pressurized with nitrogen on the backside of the piston during the discharge stroke. The 68.6 cm barrel was equipped with eight multiple use ports allowing application of vacuum, injection of aqueous ammonia, injection of steam, and insertion of thermocouples for measurement of temperature inside the barrel. The reactor barrel was equipped with a steam jacket for even heating of the barrel. The reactor barrel was directly attached to a 15.2 cm×61 cm stainless steel flash tank, oriented vertically. The barrel was isolated from the flash tank by a conical nozzle and seat end shearing valve arrangement. The diameter of the end valve shearing die was 3.5 cm. The backpressure on the conical nozzle and seat was adjustable, with most tests performed using ~138 kPa (gauge pressure) of backpressure into a 10.2 cm diameter air cylinder connected to the cone of the end shear valve. The cone of the end shearing valve could move back up to 1.6 cm to allow discharge of particles in the flash tank. An elbow at the outlet of the end shear valve directed the pretreated solids down into the bottom of the flash tank where the solids were easily removed by unbolting a domed end flange in the bottom of the tank. An upper domed flange to the flash tank incorporated a special outlet fitting with slots machined at right angles to the axis of the flash tank, which caused released vapors to travel around a corner path to an exit fitting, helping to prevent carry-over of entrained biomass particles and water droplets into a vent condenser. Three electrical band heaters (set at 60° C.) and insulation were added along the flash tank to allow hot pretreated solids to flash into a heated vessel, better simulating a commercial scale process.

Saccharification Equipment

Saccharification experiments were conducted in three types of systems.

One system was the Pretreatment and Enzymatic Hydrolysis Reactor (PEHR) that is described above and is referred to as "Roller Bottle". An alternate variation of a roller bottle system was a ceramic roller bottle with a 1.3 gallon volume (US Stoneware, East Palestine, Ohio). The attrition media, and rolling and heating systems were identical to those described for the PEHR above. Experiments in the roller bottle were always done in batch mode.

The second system consisted of stirred tank reactors, where the experiments were conducted in batch or fed batch mode. The system consisted of a glass jacketed cylindrical reaction vessel, either 500 ml or 2000 ml (LabGlass Number LG-8079C, LabGlass, Vineland, N.J.), equipped with a four neck Reaction Vessel Lid (LG-8073). A stirrer was mounted through the central port to stir the reactor contents. A glass condenser was connected to one of the necks and was kept chilled at 5° C., by recirculating water from a chiller. The other two ports were used for loading of reactants and for temperature and pH measurements. The reactor temperature was controlled by recirculating hot water, supplied by a heated circulator water bath. A Teflon® coated anchor stirrer was used in the 2000 ml reactor and a four-paddle glass stirrer with 45 degree angled paddles was used in the 500 ml reactor.

The third system consisted of a B. Braun Biotech International type 10K 15-Liter fermentor reactor, which was used as a saccharification reactor. It is controlled by a BioStat ED DCU (data control unit) and associated control module containing; circulating pump, acid and base pumps, solenoid valves, heat exchangers for temperature control, steam supply, process water, air supply control valves, filtration and back pressure control valves, and exhaust filters. The reactor was equipped with two 4.5 inch (11.4 cm) diameter three-blade high efficiency Ligntnin A-310 impellers. The bottom impeller was located 3 inches (7.6 cm) from the reactor bottom and the upper impeller was located 9 inches (22.9 cm) from the reactor bottom. The vessel has a diameter of 7.5 inches (19.1 cm) and a maximum height of 22 inches (55.9 cm). Four removable baffles were used in the fed batch saccharification runs, each of which has a width of ⅝ inch (1.6 cm) and a length of 19 inches (48.3 cm) (from the vessel bottom to within about 3 inches) 7.6 cm) of the top). There is a narrow gap of ~⅛ inch (0.3 cm) between the baffle edge and the vessel wall, but biomass does not typically get trapped in this gap. At the start of the fed batch saccharification, the slurry volume occupies about the bottom 5 inches (12.7 cm) of the vessel, which is deep enough to cover the side port near the vessel bottom used in the pump around loop when the loop is full with saccharification slurry. This initial level falls between the two impellers. During the course of the fed batch additions, the slurry level eventually rises to cover the top impeller.

The head plate of the vessel was modified to incorporate a 2 inch (5.1 cm) sanitary fitting for loading biomass and charging enzymes. In addition, an associated pump around loop was installed into the top and bottom ports on the reactor system. The pump around loop was isolated from the fermentation vessel with 1½ inch (3.8 cm) Valmicro and SVF full port ball valves with CF8M bodies, 316 SS balls, and PTFE seats. The 1½ inch (3.8 cm) flexible hoses comprising part of the pump around loop were constructed of platinum cured silicone inner hose with 316 SS wire reinforcement and silicone outer jacket with a working pressure of 150 psi, a temperature rating to 250° C., and sanitary end connections. A Teflon sight flow indicator was plumbed into the inlet of the lobe pump through sanitary fittings. Tees were incorporated in the pump around loop that allowed for direct steam injection and condensate drainage that allowed separate sterilization of the pump around loop hoses, APV lobe pump, Teflon sight glass, ball valves and V-port valve. All components in the pump around loop were separately cleaned and sterilized before aseptically assembling into the loop. In particular, the ball valves were partially opened, cleaned behind the seats, and then steam sterilized in the partially open position in an autoclave prior to assembling the pump around loop to minimize the chance that material trapped behind the seats and balls could allow contaminants to survive sterilization and infect the fermentation. After connection of all pump around loop components were made, the pump around loop and components were again sterilized with steam in place a second time.

The pump around loop centered around an APV lobe pump. The APV lobe pump (model M1/028/06) constructed of 316 SS was powered by a 3-hp Reliance Electric motor coupled to the lobe pump through a Dodge Master XL speed reducer. The motor rpm of 1755 rpm was reduced by the Dodge right angle speed reducer with a gear reduction of 5:1 coupled to the lobe pump. The Reliance Electric motor was controlled by a Reliance SP500 variable frequency drive. The lobe pump was rated at 85 psig at 960 rpm. Connections of the pump to the external pump around loop were through sanitary fittings. The lobe pump was sterilized in place by running the lobes slowly while exposing the internals of the pump to 30 psig steam pressure. The pump was run in the forward direction that allowed pumping of any condensate formed in the pump to the steam trap located on the discharge end of the pump piping. A sanitary type diaphragm isolated pressure gauge was used to monitor steam pressure during sterilization, as well as pump pressure during the pump around and V-port valve shearing cycles.

The V-port shear valve was incorporated into the pump around loop and found down stream of the lobe pump just prior to the ball valve isolating the pump around loop from the top port of the fermenter. The Triac Controls "V" 88 series control port ball valve was ordered with a 1½ inch (3.8 cm) ball and body with a 60° Vee notch in the ball. The body of this valve is constructed of CF8M SS rated to 1500 psig, with 316 SS 600 V-port ball and PTFE seats. The threaded connections in the body of the V-port valve were connected to the pump around loop using 1½ in (3.8 cm) threaded pipe to sanitary connectors.

Example 1

Saccharification of Pretreated Biomass with and without Stirring

Two runs (#25 and 26) were conducted with milled pretreated biomass at 50° C., pH=5.5 with about 20% DWB (Dry Weight of Biomass) loading. The biomass used in these runs was a blend of three batches of pretreated corn cobs that were size reduced to about 1 mm. One batch, labeled HT-4, was prepared in the steam gun reactor, described above, by treating the fractured corn cobs with 4 g $NH_3$ per 100 gram of dry weight biomass and steam at 145° C. for 20 minutes. The other two batches were prepared in the Barrel Piston reactor, described above, by treating the corn cobs with 6 g $NH_3$ per 100 gram of dry weight biomass and steam at 145° C. for 10 minutes. The blend of these three batches of pretreated biomass was ground in a Waring commercial blender and screened through a 1.1 mm screen, before using in the saccharification experiments.

The runs were conducted in 500 mL glass jacketed cylindrical reaction vessels, described in General Methods. The heel consisted of about 100 g de-ionized water and about 100 g of a saccharified hydrolysate from a previous run, which was added to help increase the solids content of the final hydrolysate. After increasing the temperature to 50° C., the pH was adjusted to 5.5 and about 180 g of the ground pretreated biomass was added. The percent dry weights of biomass in the final hydrolysates were 20.97% and 17.83% in Runs 25 and 26, respectively.

Enzymes added to each reactor were Spezyme® CP (Genencor International, Rochester, N.Y.) at 10 mg of protein/g cellulose and Multifect® Xylanase (Genencor) at 4.1 mg of protein/g hemicellulose. In Run-25, after the initial mixing of ingredients for about 30 minutes the stirrer was stopped, whereas in Run-26 the stirrer was kept running at 500 rpm. The sugar content of the resulting saccharification liquor was determined after 17 hr saccharification according to the sugar measurement protocol described in the General Methods. Sugar release after 17 hr is given in Table 1.

Run 25 showed that the enzymes saccharified the cellulose and hemicellulose even without stirring. However, the amounts of sugar formed in Run 26 were higher than in Run 25, indicating that the rate of saccharification was faster in the stirred reactor. Saccharification rate of glucan to total glucose and to glucose monomer was about 50% faster in the stirred reactor than in the stagnant reactor.

TABLE 1

Formation of various sugars at 17 hours after addition of enzymes

| Run No. | Stirrer, rpm | DWB % | Total Glucose, g/L | Glucose Monomer, g/L | Total Xylose, g/L | Xylose Monomer, g/L |
|---|---|---|---|---|---|---|
| 25 | 0 | 20.97 | 30.08 | 16.03 | 33.54 | 9.78 |
| 26 | 500 | 17.83 | 43.99 | 23.69 | 39.13 | 9.39 |

This example clearly showed that a faster and a more cost effective saccharification process would require continuous stirring of solids in the reactor mixture.

During saccharification, the insoluble cellulose and hemicellulose were converted to water-soluble glucose, xylose and their oligomers. As the reaction progressed, the fraction of insoluble solids decreased and the amount of liquid increased. Furthermore, the size distribution of particles also decreased, as measured following procedures in General Methods. The median size of particles (d-50) decreased from 614 micrometers in the feed to 309 micrometers in Run 25, while it decreased to 113 micrometers in Run 26, again confirming that stirring increased the rate of solubilization of solids.

Example 2

Saccharification of Pretreated Biomass with Varying Initial Size

Runs 50-52 and 64-65 were conducted with pretreated biomass milled to different sizes. The pretreated biomass was prepared from crushed corn cobs that were hammermilled and screened through a ½ inch screen. They were treated in the Jaygo Reactor, described in General Methods, with 4 g $NH_3$ per 100 gram of dry weight biomass and steam at 145° C. for 20 minutes. This pretreated corn cob biomass was labeled Jaygo-10. Before saccharifying, the pretreated corn cobs were further milled in multiple steps and screened through appropriate size screens to prepare the biomass for each saccharification run. The screen size used for preparing samples for each run is shown in Table 2 below.

Runs 50 and 51 were conducted in 2-L reactors and Runs 52, 64 and 65 were conducted in 0.5 L reactors. In all cases, de-ionized water was used as the reaction heel. Pretreated biomass was added to make hydrolysates of about 12% DWB in Runs 50-52 and about 21% DBW in Runs 64 and 65. The temperature was increased to 50° C. and the pH was adjusted to 5.5 with phosphoric acid. In runs 50-52, Spezyme® CP was loaded at 40 mg protein/g cellulose and Multifect® Xylanase was loaded at 15.6 mg/g hemicellulose. In runs 64 and 65 Spezyme® CP was loaded at 35.4 mg protein/g cellulose and Multifect® Xylanase was loaded at 14.4 mg/g hemicellulose. The reactors were continuously stirred at 300-500 rpm to maintain the particles suspended and well stirred. After 72 hours, the sugar content of the resulting saccharification liquor was measured according to the sugar measurement protocol described in the General Methods and the results are shown in Table 2 as percent of theoretical yield.

There was a clear relationship between the particle size of the pretreated biomass and the yield of sugars formed in saccharification, as shown in Table 2, smaller size initial cob particles yielded higher amounts of sugars.

TABLE 2

Percent of Theoretical yield at 72 hours after addition of enzymes

| Run No. | Initial Particle Size | Glucose Monomer | Glucose Total | Xylose Monomer | Xylose Total |
|---|---|---|---|---|---|
| Run 50 | <10 mm | 38.1 | 41.4 | 20.6 | 35.9 |
| Run 51 | <6.2 mm | 58.3 | 64.6 | 34.4 | 60.3 |
| Run 52 | <1.12 mm | 78.8 | 86.2 | 52.4 | 76.6 |
| Run 64 | <1.12 mm | 80.5 | 88.8 | 47.7 | 84.7 |
| Run 65 | <0.5 mm | 77.0 | 95.7 | 46.8 | 90.1 |

Run 64 is a replicate of Run 52 and shows the reproducibility of runs.

The particle size distribution of the product hydrolysate after 72 hours was determined for each run and the results are given in Table 3. Runs with smaller initial particle size had smaller particles in the product hydrolysate. These results confirmed that size reduction facilitates saccharification and showed that higher yields were attained with finer particles, such that 90-95% yields of saccharification were obtained with final particle sizes with d-95 of less than 75 micrometer.

TABLE 3

Particle Size Distribution of Product Hydrolysates

| Run No., | Initial Particle Size | Hydrolysate d-50 micrometer | Hydrolysate d-95 micrometer |
|---|---|---|---|
| Run 50 | <10 mm | 29.7 | 484 |
| Run 51 | <6.2 mm | 116 | 560 |
| Run 52 | <1.12 mm | 17.1 | 136 |
| Run 64 | <1.12 mm | 20.3 | 158 |
| Run 65 | <0.5 mm | 12.9 | 74.7 |

These experiments showed that saccharification rate is a mass transfer controlled phenomenon. Therefore, a high yield of over 90% at fast rate can be attained if the particles in hydrolysate are reduced in size to less than about 75 micrometer.

Example 3

Liquefaction of Biomass During Enzymatic Saccharification

Run 52, described above, was also used to determine the changes in particle size distribution and the liquefaction of biomass as the saccharification process continued. The particle size distributions were measured for the initial milled pretreated corn cob biomass and for the hydrolysate after 6 and 72 hours.

TABLE 4

Reduction of particle size distribution during saccharification - Run 52

| Run Time | Hydrolysate d-50 micrometer | Hydrolysate d-95 micrometer |
|---|---|---|
| 0 hr | 177.5 | 1020.8 |
| 6 hr | 38.9 | 163.5 |
| 72 hr | 17.1 | 136 |

This result clearly indicated that enzymatic saccharification reduces the size distribution of the solid particles, thus causing liquefaction of solids, opening room for additional solids to be added to the hydrolysate.

Example 4

Determining Solids Loading Limitation

The economics of a lignocellulose-to-ethanol process is favorable when there is a high concentration of sugars in saccharification hydrolysates for use in fermentation. This requires saccharifiers to operate with high concentrations of solids. Runs 43-45 were conducted to determine the operating limitations of high solids loading in the saccharification reactor.

Run 43 was conducted in a 500 ml reactor with pretreated corn cobs, milled and screened through 1.12 mm mesh. The milled cobs were added incrementally to 200 g of the water heel in the reactor and stirred. At each stirring speed, starting with 100 rpm, the biomass was added to determine visually the point where the biomass solids would stagnate and stop moving with the bulk of fluid. Addition of about 13.6% DWB caused stagnation at 100 rpm. The process was continued at higher stirring speeds of 200, 300 and 500 rpm, reaching stagnations at 13.8%, 15.5%, and 15.7% DWB, respectively. Initially, all of the biomass dispersed in the water and stirred well with the agitator. As the percent dry weight of biomass reached about 13.8% at 100 rpm, a portion of the solids separated from the agitating mixture and accumulated in the bottom of the reactor. By increasing the speed of rotation, more biomass could be added and maintained in mixing. However, as the stirring speed reached 500 rpm, the % DWB that could be added without stagnation reached a plateau of about 15.7%, as shown in FIG. 1.

In Run 46, the biomass loading capacity test was repeated with particles that were milled and screened through 6.2 mm mesh. The coarse solids showed a behavior similar to finer particles of Run 43, and started to separate from mixing mass and stagnate at the bottom of the reactor as the % DWB increased. As FIG. 1 shows, the coarse particles were more prone to stagnation than the finer particles. For both fine and coarse particles, 15.7% DWB appeared to be the limit of solids loading. This percent solids is the limit for the reactor and impeller geometry used in this experiment and its value would be different with other systems. However, in all geometries and impeller arrangements a certain percent solids is expected to be the limiting factor for proper mixing.

This example shows that in a batch mode of operation, where the entire load of biomass is added at the beginning of a batch, there is a limit of about 16% on the percent of dry weight of biomass, above which the solids will start to stagnate. While Example 1 showed that even in a non-stirring mixture, the enzymatic saccharification can proceed slowly, but on a large industrial scale, one cannot easily mix the biomass and enzymes to start the slower saccharification. Thus, an approximate 16% DWB becomes a limit for batch operation. Furthermore, in a large tank reactor, if the biomass were allowed to stagnate, its re-suspension into the slurry would require large amounts of energy.

Example 5 pH Control with Fed Batch Saccharification

Example 4 demonstrated that at DWB higher than about 16%, part of the biomass separated form the slurry and became stagnant. In the absence of adequate mixing, the pH of the pretreated solids cannot be adjusted. Even with difficult to mix slurries, the localized variations in pH could be detrimental to enzymatic saccharification. While the optimum pH range for each enzyme could be different, most saccharification enzymes have an optimum pH of 5 to 5.5. The enzymes require a tight pH control to perform effectively.

Runs 96-99 were conducted to determine the sensitivity of enzymes to pH variations. These runs were made with pretreated corn cobs designated as Jaygo-10, which were prepared in the Jaygo Reactor, described above, with 4 g $NH_3$ per 100 gram of dry weight biomass and steam at 145° C. for 20 minutes. Before saccharifying, the pretreated biomass was further milled in a hammermill and screened through 1.12 mm screen. The runs were made in batch mode in 500 ml reactors with % DWB of 13.1 to 14.5%, thus the mixing was always uniform, as observed visually. All four runs were started at pH=5.5 and at 50° C., with Spezyme® CP loading of 35.4 mg/g cellulose and Multifect® Xylanase loading of 14.4 mg/g hemicellulose. Two hours after the start of each run, the pH was adjusted to a new value and maintained for one hour. The pH of Run 97 was kept at 5.5 but the pH of Runs 96, 98, and 99 were adjusted to 4.0, 6.5 and 7.5, respectively.

After one hour, the pH was then readjusted to its original 5.5 and the runs continued for 48 hours. Table-5 shows the yields of various sugars at 48 hours. The results clearly indicated that the enzyme activity was sensitive to pH fluctuations, with production of glucose and xylose monomer being the most sensitive.

TABLE 5

Effects of One Hour pH Shift on Yields

| | | Percent Yield of Sugars | | | |
| --- | --- | --- | --- | --- | --- |
| Run No. | pH shift | Glucose Monomer | Glucose Total | Xylose Monomer | Xylose Total |
| 96 | 4.0 | 49.6 | 60.3 | 33.2 | 62.1 |
| 97 | 5.5 | 67.8 | 81.5 | 41.8 | 75.5 |
| 98 | 6.5 | 58.6 | 69.5 | 36.4 | 66.9 |
| 99 | 7.5 | 43.2 | 54.0 | 26.0 | 64.1 |

This example confirms that adequate mixing is required in order to maintain the pH in the optimum range for saccharification of a high solids loading hydrolysate.

Example 6

Increased Solids Loading with Fed Batch Saccharification

Figure 2:
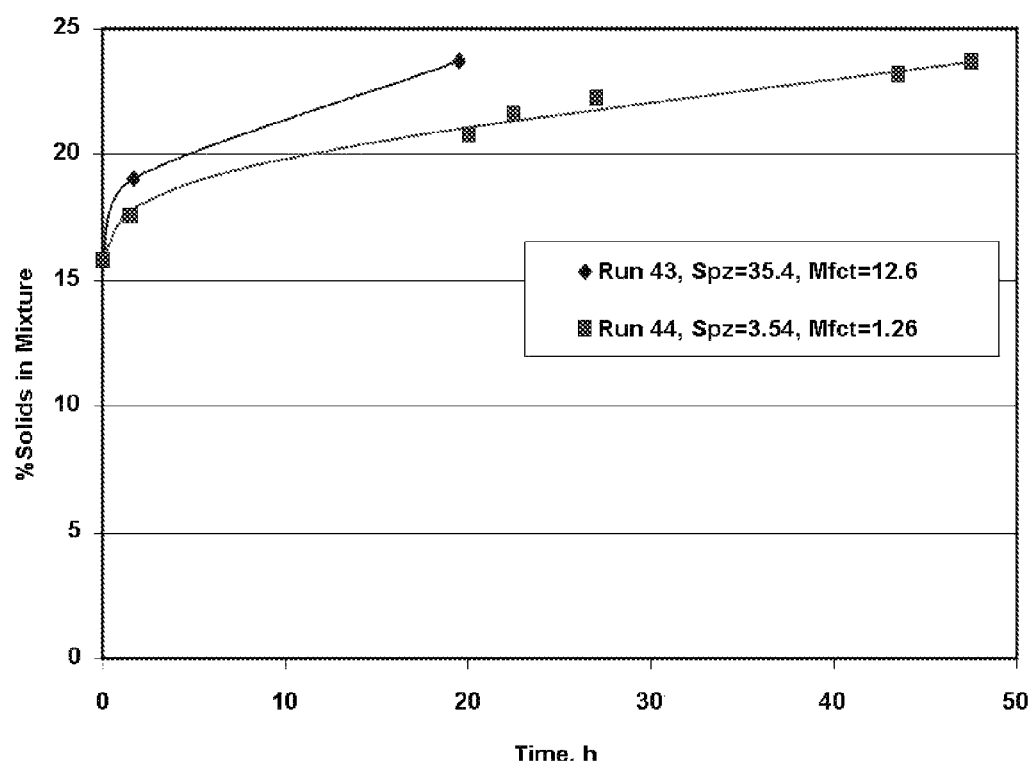
FIG. 2 shows a graph of the effect of different amounts of enzyme loading on reducing corn cob biomass stagnation.

Run 43 (described in Example 4), after reaching its critical solids level for flowability of 15.7% DWB, was continued and saccharified at pH=5.5 and 50° C., with Spezyme® CP loading of 35.4 mg/g cellulose and Multifect® Xylanase loading of 14.4 mg/g hemicellulose. As FIG. 2 shows, within two hours the mixture became fluid again and all of the solids started stirring in the reactor. More milled pretreated corn cob biomass of <1.12 mm was added to the reactor contents, which increased the total % DWB in the reactor to about 19% before the solids separated again. The solids in the reactor contents was based on the % of material added as solids in the final volume of the reactor contents. After 18 hr, the reactor contents were stirring again and more corn cob biomass of <1.12 mm was added to bring the total solids concentration to 23.7%, while the reactor contents remained in a stirring state. Thus during the enzymatic saccharification it was possible to feed pretreated and milled corn cob biomass in a semi-batch or fed batch mode to reach an increased level of solids in the saccharification reaction.

Run 44 was conducted using conditions identical to those of Run 43, except that the enzyme loadings were 10 times lower than those in Run 43. As FIG. 2 shows, again enzymatic saccharification led to solids liquefaction, allowing more solids to be added in fed batch mode to the reactor contents while maintaining stirring state. However, at lower enzyme loading, the rate of liquefaction was slower, thus the rate of addition of solids was slower, such that with 0.1-fold of enzyme loading it took 48 hours to load solids to increase the percent solids to 24% while maintaining a stirred state of the reactor contents.

This example clearly indicates that combined enzymatic saccharification, proper mixing and fed batch process allows high biomass concentrations (% DWB) to be reached in the saccharifier, while maintaining all the solids in a stirred state.

Example 7

Viscosity and Yield Stress in High Biomass Solids Hydrolysates

The hydrolysate is a non-Newtonian slurry and its viscosity changes with biomass loading, extent of saccharification, the applied sheer, as well as temperature. Runs 149-152 were conducted with various levels of % DWB and the samples collected at different times to measure the rheological characteristics of the hydrolysates. These runs were conducted in the 2 liter reactor with pretreated corn cobs. The fractured corn cobs were pretreated in the Jaygo Reactor, described above, with 6 g $NH_3$ per 100 gram of dry weight biomass and steam at 145° C. for 20 minutes, and the sample was designated as Jaygo-9. The pretreated cobs were further milled to less than 1.12 mm size before use in the saccharifier. The saccharifications were conducted at 50° C. and pH=5.5, with Spezyme® CP loading of 35 mg protein/g cellulose and Multifect® Xylanase loading of 15 mg protein/g hemicellulose.

Figure 3:
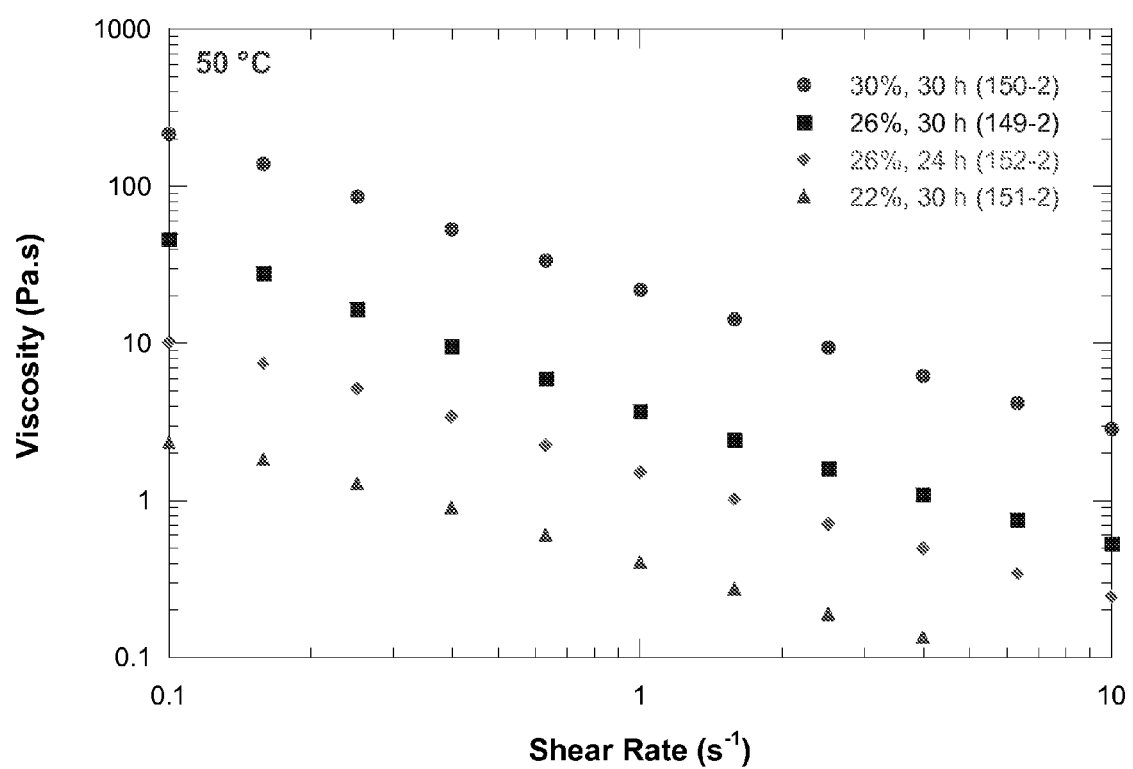
FIG. 3 shows a graph of the variation of viscosity of hydrolysates with % DWB.

Viscosity was measured with changing sheer rate as described in General Methods for hydrolysate samples taken at 30 hours after addition of enzymes for 22%, 26%, and 30% of dry weight biomass, and at 24 hours for the 26% sample. The data shown in FIG. 3 clearly indicates that the hydrolysates are shear thinning Non-Newtonian fluids. FIG. 3 also shows that viscosity depends strongly on the % DWB in the hydrolysate, varying by two orders of magnitude when the % DWB is increased from 22% to 30%.

Figure 4:
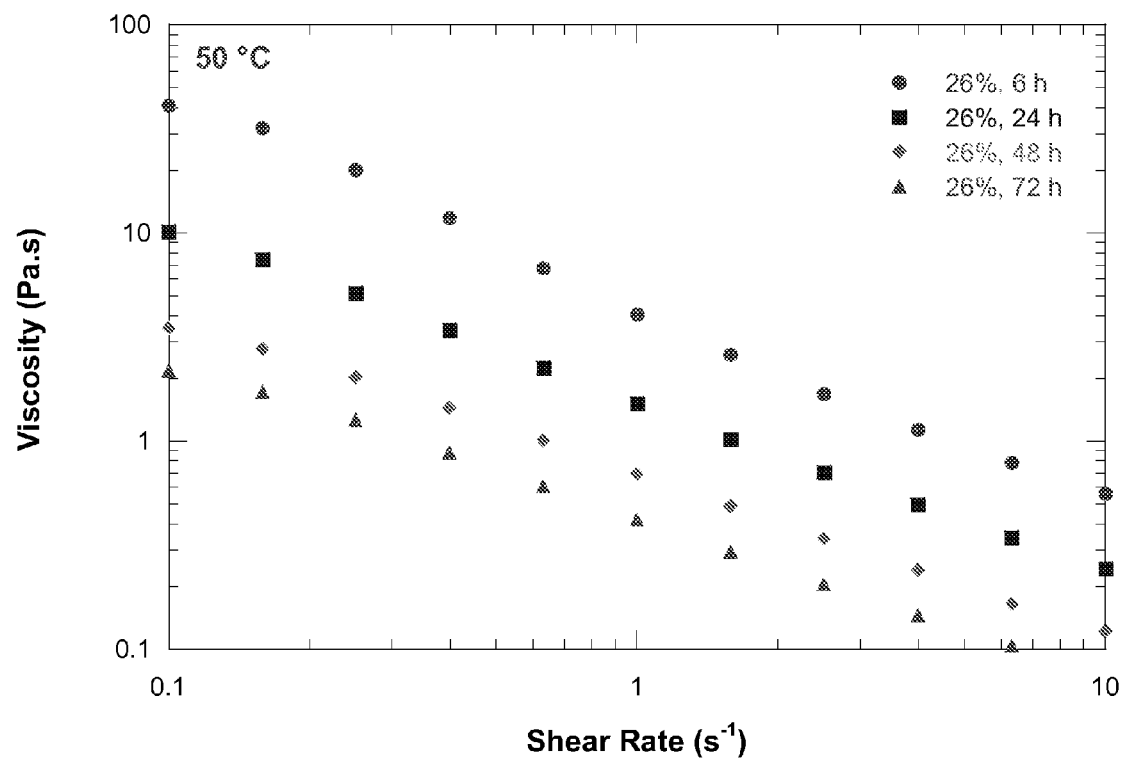
FIG. 4 shows a graph of the effect of saccharification reaction time on viscosity.

For the 26% solids sample, viscosity was measured with changing sheer rate for hydrolysate samples taken at 6, 24, 48, and 72 hours after addition of enzymes. The results given in FIG. 4 show the effect of time or extent of saccharification on the viscosity. The hydrolysate with 26% solids had a very high viscosity even 6 hours after saccharification and its viscosity continuously decreased with time as the enzymes saccharified the cellulose and hemicellulose, and decreased the volume of undissolved solids in the hydrolysate.

Further analysis of these data using a Herschel-Bulkley model show that a hydrolysate with 26% solids has a yield stress during the first 24 hours of saccharification. Table 6 shows the Herschel-Bulkley model parameters and specifically the yield stress indicated by $\sigma_{HB}$. Experimentally, the yield stress is observed by stagnation of the reactor contents specifically near the walls.

TABLE 6

Herschel-Bulkley Parameters for 26% DWB Hydrolysates
$\sigma = \sigma_{HB} + K_{HB}\gamma^q$

| Sample | Solids | Reaction Time | $\sigma_{HB}$ (Pa) | $K_{HB}$ (Pa) | q (—) |
| --- | --- | --- | --- | --- | --- |
| 152-1 | 26% | 6 h | 3.4 | 1.17 | 0.066 |
| 152-2 | 26% | 24 h | 0.52 | 1.02 | 0.260 |
| 152-4 | 26% | 48 h | 0.0 | 0.687 | 0.248 |
| 152-6 | 26% | 72 h | 0.0 | 0.425 | 0.256 |

Example 8

Super High Biomass Solids Saccharification

Run 63, was conducted to demonstrate saccharification at a much higher biomass concentration than is currently envisioned for an economical process. The as-received pretreated corn cobs designated as Jaygo-10, as described in Example 2 above, contained about 36% DWB. After milling to 1.12 mm size, they were air-dried to reduce their moisture content to less than 11%. This material was saccharified in fed batch mode in the 500 ml reactor, at pH=5.5 and 50° C., with Spezyme® CP loading of 35.4 mg protein/g cellulose and Multifect® Xylanase loading of 14.4 mg protein/g hemicellulose. Initially 44.55 g of pretreated biomass (about 36% of the total solids of the run) were added to 170 g heel water and the stirrer was started at 500 rpm. After adjusting the pH, the enzymes required for this amount of pretreated biomass were added. The biomass was at the verge of stagnation and was stirring very slowly near the reactor wall, while it was stirring rapidly at the center near the stirrer. After about 30 minutes, some biomass had liquefied, allowing the biomass in the reactor to stir reasonably well, including near the reactor wall. At this time, about 17% more of the total pretreated biomass was added, the pH adjusted, and corresponding amounts of enzymes were added, moving the reactor to the verge of stagnation. After 1 hour and 15 minutes, the reactor contents were stirring well. An additional 17% of the pretreated biomass was added along with corresponding amounts of acid and enzymes. After another 3 hr and 15 min, the reactor was stirring reasonably well, then the remaining 30% of the total biomass was added. After adjusting the pH and adding the enzymes, the reactor contents were mostly stagnant. After 16 hours, the reactor contents were stirring slowly, primarily due to high viscosity of the mixture. The run continued for a total of 77 hours after the initial loading of enzymes.

This fed batch process allowed a hydrolysate of 38.09% DWB to be prepared with 55% yield to glucose and 58% yield to xylose. The hydrolysate contained 108 g/L of glucose and its oligomers, and 99 g/L of xylose and its oligomers, for a total of 207 g/L of soluble sugars. The milled and pretreated biomass and the enzymes were added in fed batch mode in a total of 5 hours. In this laboratory test, only the last addition of biomass caused stagnation in the reactor for about 10-16 hours, which could have easily been avoided had the last charging of solids been done in two increments within the 10-16 hours. At these high solids loading, the viscosity of the hydrolysate became quite high and posed fluid handling challenges.

Example 9

Effects of In-Situ and External Grinding on Saccharification

Examples 1-8 above demonstrate the need for particle size reduction to achieve high saccharification yields and high % DWB loading. The biomass used in these examples had been milled before the start of saccharification. It would be more economical for a scaled-up process to achieve particle size reduction by in-situ grinding. A commercial process is envisioned to have a recirculation loop with an in-line grinder in the loop. In order to test the effectiveness of various types of grinders, runs 115F, 116F, 117F, 118F and 125F were conducted using different grinding arrangements.

The pretreated biomass used in these runs was a mixture of 40% cobs and 60% fiber by dry weight of solids. Fiber refers to the external layer covering corn kernels, also known as the corn hull. It is a lignocellulosic biomass, like cobs, which, additionally contains starch and can be used in the saccharification process. This 40/60 cob/fiber mixture was pretreated in the Jaygo Reactor, described in General Methods, with 6 g $NH_3$ per 100 gram of dry weight biomass and steam at 145° C.

for 20 minutes. This pretreated corn cob/fiber mixture was labeled DTM-17. Before saccharifying, the pretreated biomass was further milled in a hammermill and screened through a 1.12 mm screen.

This material was saccharified in fed batch mode in the 500 ml reactor, at pH=5.5 and 50° C. The biomass was charged in three batches over 6 hours. The % DWB of these runs varied from about 23% to about 28%. The enzymes were also added in fed batch mode with Spezyme® CP loading of 12.9 mg/g cellulose and Multifect® Xylanase loading of 15.0 mg/g hemicellulose and Spirizyme® B4U (Novozymes North America, Franklinton, N.C.) of 1 mg/g starch.

Run 115F was a reference run, with no additional size reduction during saccharification. The reactor contents were stirred with the standard stirrer described above at 500 rpm throughout the run. All five runs 115F, 116F, 117F, 118F and 125F were conducted for a total of 72 hours. In Run 116F, a hand-held Roto-stator (Ultra-Turrax T25 s$^{-1}$ with T-18 head, IKA Works, Inc., Wilmington, N.C. 28405) was used to grind the biomass in-situ at 20,500 rpm. The is-situ grindings were done at 25, 26.5, 45, 47, and 49 hours after addition of the first enzyme. The roto-stator was run for 10 minutes each time, with intermittent stoppage to prevent any overheating of the Rotostator or the hydrolysate. In Run 117F, the contents of the reactor was transferred to a Waring blender, cooled to about 30° C., and each time, the blender was run for 10 minutes in 2 minutes intervals. Then the hydrolysate was returned to the reactor to continue the saccharification. This process was done five times at 22, 26, 46, 50, and 69 hours after addition of the first enzyme. In Run 118F, the process of Run 117F was repeated, except that the blender was run for 30 minutes each time. This process was done five times at 23, 27, 47, 51, and 70 hours after addition of the first enzyme. In Run 125F, the regular stirrer, described above, was replaced with a High Sheer Disperser (R1300 Dissolver Stirrer, IKA Works, Inc., Wilmington, N.C. 28405) that was run at 500 rpm with intermittent increase of stirring speed to 900 rpm for the duration of the experiment.

The yields of saccharification and particle size reduction results are shown in Table 7. The particles size distribution (PSD) of the feed biomass was reduced by a factor of about three in the reference saccharification Run 115F, without any additional grinding. Grinding in the Waring blender showed further reduction in d-50 and d-95, but only slight improvements in the saccharification yields. However, using the roto-stator or replacing the regular stirrer with a High Sheer Disperser reduced the particle size distribution further and increased the saccharification yield. While the sheer disperser may not be a viable option for scale-up, a roto-stator placed in an external recycle loop is a promising less-expensive option for particle size reduction.

TABLE 7

Effects of Various Grinding Methods on PSD and Yields

| Run Number | Stirring | Particle Size, micrometer | | Percent Yield | | | |
|---|---|---|---|---|---|---|---|
| | | d-50 | d-95 | Glucose Monomer | Total Glucose | Xylose Monomer | Total Xylose |
| DTM-17 Milled to 1.12 mm | — | 71.3 | 494.0 | — | — | — | — |
| 115F | No additional Grinding | 27.8 | 175.3 | 54.0 | 70.0 | 28.2 | 84.9 |
| 117F | Waring Blender, 50 min | 20.9 | 47.7 | 55.9 | 71.8 | 27.3 | 85.6 |
| 118F | Waring Blender, 2 h and 30 min | 17.0 | 73.8$^a$ | 54.7 | 72.1 | 27.1 | 85.5 |
| 125F | High Sheer Disperser | 8.0 | 30.8 | 64.2 | 80.1 | 33.9 | 93.6 |
| 116F | RotoStator, 10 min | 21.0 | 42.9 | 63.7 | 83.7 | 33.8 | 103.2 |

$^a$This number is thought to be a sampling error, with the d-50 data providing an accurate number.

Example 10

Saccharification with Particle Size Reduction in an External Loop Grinder

Run 163 was conducted by taking hydrolysate out of the saccharifier and grinding it in a loop reactor equipped with an in-line ½ hp roto-stator grinder (Charles Ross and Son Co., Hauppauge, N.Y. 11788). Corn cobs were pretreated in the Jaygo Reactor, described above, with 4 g NH$_3$ per 100 gram of dry weight biomass and steam at 145° C. for 20 minutes, labeled as Jaygo-9. The pretreated biomass was milled to 1.12 mm size and used in this test. This material was saccharified in the 500 ml reactor, at pH=5.5 and 50° C. The biomass was charged in one batch, mixed with a spatula, pH adjusted and enzymes added with Spezyme® CP loading of 20.0 mg/g cellulose and Multifect® Xylanase loading of 10.0 mg/g hemicellulose. The % DWB biomass loading was 25.76%. The mixture was very viscous and stirred only at the core, near the stirrer.

Twenty hours after allowing the solids to soak in the enzyme, to saccharify partially, the contents of the reactor were transferred to a tank connected to the in-line grinder. The grinder was run at 3600 rpm twice in three-minute intervals, for a total of six minutes. The hydrolysate was returned into the reactor and run under saccharification conditions for an additional 4 hours. Table 8 shows the sugar analysis of hydrolysate before and 4 hours following this grinding step. An external grinding showed a strong positive effect on saccharification, specifically on formation of glucose monomer and glucose total, which increased by 61 and 44%, respectively.

TABLE 8

Effect of External Roto-Stator Grinding on Saccharification

| | Time from enzyme loading, hr | Titer of Sugars, g/L | | | |
|---|---|---|---|---|---|
| | | Glucose Monomer | Total Glucose | Xylose Monomer | Total Xylose |
| Before Grinding | 20 | 29.73 | 45.02 | 29.32 | 69.88 |
| After grinding and 4 hr saccharification | 25 | 47.91 | 64.96 | 34.51 | 73.03 |

Example 11

Effect of Enzyme Addition Strategy on Saccharification

Saccharification in the fed batch mode allows an opportunity to optimize the addition of various enzymes to find the best strategy for enzyme addition to gain the highest saccharification yields. Runs 164 through 167 were conducted as one set of tests to analyze this optimization process. These runs were conducted in the 500 ml reactor with pretreated corn cobs. The fractured corn cobs were pretreated in the Jaygo Reactor, described above, with 4 g $NH_3$ per 100 gram of dry weight biomass and steam at 145° C. for 20 minutes, and was designated as Jaygo-9. The pretreated cobs were further milled to less than 1.12 mm size before use in the saccharifier. The saccharifications were conducted at 50° C. and pH=5.5, with Spezyme® CP loading of 20 mg protein/g cellulose and Multifect® Xylanase loading of 10 mg protein/g hemicellulose. The enzymes were added using different regimes as listed in Table 9. At 54 or 142 hours of saccharification, samples were taken and the sugars were analyzed. The results given in Tables 9 and 10 show that saccharification of cellulose was favored when both cellulases (Spezyme® CP) and hemicellulases (Multifect® Xylanase) were added at the beginning, suggesting a synergistic interaction. However, formation of xylose monomer was improved when hemicellulase was added first followed by the cellulase. This example only shows the potential for optimization and does not necessarily represent an optimum enzyme addition strategy.

TABLE 9

Effect of Enzyme Loading on Yields of Saccharification at 54 hr

| Run No. | Enzyme Loading | Yield at 54 hr g/liter | | | |
|---|---|---|---|---|---|
| | | Glucose Monomer | Glucose Total | Xylose Monomer | Xylose Total |
| 164 | All Enzymes at t = 0 | 51.5 | 65.7 | 37.8 | 73.0 |
| 165 | Spezyme ® CP at t = 0, Multifect ® Xylanase at t = 22 h | 41.8 | 54.0 | 34.5 | 70.6 |
| 166 | Multifect ® Xylanase at t = 0, Spezyme ® CP at t = 22 h | 39.2 | 41.8 | 38.9 | 61.4 |
| 167 | ½ Enzymes at t = 0, ½ Enzymes at t = 22 h | 36.5 | 49.0 | 34.5 | 68.4 |

TABLE 10

Effect of Enzyme Loading on Yields of Saccharification at 142 hr

| Run No. | Enzyme Loading | Yield at 142 hr g/L | | | |
|---|---|---|---|---|---|
| | | Glucose Monomer | Glucose Total | Xylose Monomer | Xylose Total |
| 164 | All Enzymes at t = 0 | 67.9 | 79.1 | 45.5 | 78.6 |
| 165 | Spezyme ® CP at t = 0, Multifect ® Xylanase at t = 22 h | 61.7 | 73.5 | 43.2 | 77.5 |
| 166 | Multifect ® Xylanase at t = 0, Spezyme- CP at t = 22 h | 64.9 | 72.7 | 47.4 | 78.2 |
| 167 | ½ Enzymes at t = 0, ½ Enzymes at t = 22 h | 64.1 | 72.3 | 48.5 | 78.6 |

Example 12

Scale-Up of External Grinding During Saccharification

The saccharification with external grinding loop was scaled-up to a 15-liter reactor, using a lobe-pump and a sheer valve as a means to reduce the size of biomass particles and the run is denoted as SOT-06-B.

Fractured corn cobs were pretreated in the Barrel Piston Reactor, described above, with 6 g $NH_3$ per 100 gram of dry weight biomass and steam at 145° C. for 10 minutes. A total of 17 such pretreatments were carried out. Pretreated cobs from four pretreatments were pooled for saccharification to provide initial heel for the fed batch saccharification. Pretreated cobs from the remaining 13 runs were pooled for use in the fed batch saccharification.

To start the fed batch saccharification, the fed batch saccharification reactor described in General Methods was first loaded with heel hydrolysate to fill the reactor volume up to the bottom of the first impeller. This heel hydrolysate was prepared by saccharifying pretreated cobs in 2.8-L shake flasks. These shake flasks were loaded with 465 g pretreated solids, 1000 ml Di water, and enzymes at 28.4 mg Spezyme® CP/g cellulose and 4.2 mg active protein/g cellulose hemicellulase enzyme consortium (Diversa, now Verenium Corp., Cambridge, Mass.) comprising beta-glucosidase, xylanase, beta-xylosidase and arabinofuranosidase. Prior to enzyme addition, pH was adjusted to 5 with 8.5% $H_3PO_4$. The shake flasks were maintained at 50° C. and 150 rpm in a rotary shaker for 48 hr, at which time the hydrolysate was loaded into the fed batch reactor.

Once the heel hydrolysate was loaded, an aliquot of the pretreated biomass-ammonia mixture (~700 g) was added to the reactor. The pH was adjusted to a setpoint of 5.5 by addition of 8.5% $H_3PO_4$. Once the pH readjusted to the setpoint, 28.4 mg of Spezyme® CP/g cellulose and 4.2 mg active protein/g cellulose of hemicellulase enzyme consortium (Diversa) comprising beta-glucosidase, xylanase, beta-xylosidase and arabinofuranosidase were added. Additional aliquots of the same pretreated biomass-ammonia mixture, Spezyme® CP cellulase and hemicellulase enzyme consortium were added at t=4, 8, 12, 22, 26, 30 and 34 hr. The pH was adjusted to the setpoint of 5.5 by addition of 8.5% $H_3PO_4$ after each biomass addition The pump around loop was generally started about 1 hr after enzyme addition and was run for about 1 hr up through the 22 hr solids addition. After the 26 hr and 30 hr additions, the pump was started about 50 min after enzyme addition and run for 30 minutes. After the 34 hr addition, the pump was started ~3 hr after enzyme addition and run for 30 minutes. The pump was also run for 30 minutes at t=29, 33, 47 and 49 hr. Total saccharification time was 120 hr. At this time, hydrolysate contained ~60 g/L monomer glucose, 25 g/L monomer xylose and 10 g/L acetic acid. The % DWB in the hydrolysate was 24.7% and the yields of glucose monomer, total glucose, xylose monomer, and total xylose were 60.9%, 84.7%, 28.2%, and 76.6%, respectively.

Overall, Example 12 demonstrated saccharification in a tank reactor equipped with an in-line grinder in a circulating loop with high success.

Example 13

Production of Ethanol Using Saccharification Hydrolysate from Pretreated Biomass with Inhibitors in Liquid Removed Steam was added to the jacket of the barrel to preheat the barrel of the large barrel piston reactor (described in General Methods) to ~130° C. The flash receiver was preheated to ~60° C. with band heaters. Fractured cobs were prepared as follows. Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen to fracture the whole cobs into smaller pieces. These processed cobs (175 g, dry weight basis) were loaded into the large barrel piston reactor by hand placing of cobs into the end of the reactor with the piston removed. The piston was replaced to plug the end. A vacuum was applied to the reactor vessel and to the flash receiver to bring the pressure down <10 kPa, and dilute ammonium hydroxide solution was injected into the reactor to give an ammonia concentration of 6 g/100 g dry weight of biomass and a dry weight of biomass concentration of 45 g/100 g total biomass-aqueous ammonia mixture. Once the ammonia was charged, steam was injected into the reactor to bring the temperature to 145° C. The mixture was held at this temperature for 10 minutes by monitoring the temperature and adding steam as necessary and then discharged into the preheated flash tank by activating the piston. Vacuum was pulled on the flash tank until the flash receiver reached ~59° C. Upon harvest from the flash receiver, free liquid was separated from the pretreated solids and not added back for saccharification. A total of 17 such pretreatments were carried out. Pretreated cobs from 4 pretreatments were pooled for saccharification to provide initial hydrolysate for the fed batch saccharification. Pretreated cobs from the remaining 13 runs were pooled for use in the fed batch saccharification.

To start the fed batch saccharification, the fed batch saccharification reactor described in General Methods was first loaded with hydrolysate to fill the reactor volume up to the bottom of the first impeller. This hydrolysate was prepared by saccharifying pretreated cobs in 2.8-L shake flasks. These shake flasks were loaded with 465 g pretreated solids, 1000 ml DI water, and enzymes at 28.4 mg Spezyme® CP/g cellulose and 4.2 mg active protein/g cellulose hemicellulase enzyme consortium (Diversa, San Diego, Calif.) comprising β-glucosidase, xylanase, β-xylosidase and arabinofuranosidase. Prior to enzyme addition, pH was adjusted to 5 with 8.5% $H_3PO_4$. The shake flasks were maintained at 50° C. and 150 rpm in a rotary shaker for 48 hr, at which time the hydrolysate was loaded into the fed batch reactor.

Once the initial hydrolysate was loaded, the first aliquot of the pretreated biomass-ammonia mixture (~700 g) was added to the reactor. The pH was maintained at a setpoint of 5.5 by addition of 8.5% $H_3PO_4$. Once the pH readjusted to the setpoint, 28.4 mg of Spezyme® CP/g cellulose and 4.2 mg active protein/g cellulose of hemicellulase enzyme consortium (Diversa) comprising β-glucosidase, xylanase, β-xylosidase and arabinofuranosidase were added. Additional aliquots of the pretreated biomass-ammonia mixture, Spezyme® CP cellulase and hemicellulase enzyme consortium were added at t=4, 8, 12, 22, 26, 30 and 34 hr. The pump around loop was generally started about 1 hr after enzyme addition and was run for about 1 hr up through the 22 hr solids addition. After the 26 hr and 30 hr additions, the pump was started about 50 min after enzyme addition and run for 30 minutes. After the 34 hr addition, the pump was started ~3 hr after enzyme addition and run for 30 minutes. The pump was also run for 30 minutes at t=29, 33, 47 and 49 hr. Total saccharification time was 120 hr. At this time, hydrolysate contained ~60 g/L monomer glucose, 25 g/L monomer xylose and 10 g/L acetic acid.

This hydrolysate was used for fermentation of *Zymomonas mobilis* strains ZW800 or ZW658 (ATCC # PTA-7858). ZW658 is a strain of *Zymomonas mobilis* that has been engineered for xylose fermentation to ethanol and is described in co-owned and co-pending U.S. Patent Application 60/847,813, which is herein incorporated by reference. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW800 is the ZW658 strain with the gene encoding glucose-fructose oxidoreductase inactivated, which is also described in co-owned and co-pending U.S. Patent Application 60/847,813.

Fermentations were carried out in sterilized 1-liter fermentors (BIOSTAT® B-DCU system, Sartorius BBI System Inc., Bethlehem, Pa., USA) with 500 ml initial working volume. Inoculum was added to the fermentor at a level of 10% (v/v) such that the $OD_{600}$~1 in the broth after addition. Hydrolysate was present at 80% or 40% (v/v), with the balance as water. Additional glucose and xylose were added to bring final concentrations in the broth to 92 g/L and 82 g/L, respectively. Broth was also supplemented with 10 mM sorbitol and 1 g/L $MgSO_4.7H_2O$. Fermentation was carried out for 72 hr at 33° C., pH 5.8 with 150 rpm agitation. Final ethanol titers for the ZW800 strain were 8 g/L in the 40% hydrolysate and 7 g/L in the 80% hydrolysate. For ZW658, the final ethanol titers were 8 g/L in 40% hydrolysate and 6.5 g/L in 80% hydrolysate.

What is claimed is:

1. A process for producing high-sugar content hydrolysate from biomass comprising:
   a) providing a portion of reaction components in a vertical stirred tank reactor having a particle size reduction mechanism, said reaction components comprising:
      i) a portion of a mixable pretreated biomass slurry; and
      ii) a saccharification enzyme consortium comprising at least one enzyme capable of hydrolyzing cellulose;
   b) reacting said slurry and enzymes under suitable conditions;
   c) applying the particle size reduction mechanism;
   d) adding an additional portion of pretreated biomass producing a higher solids biomass slurry;
   e) optionally adding an additional portion of (ii) or another saccharification enzyme consortium comprising cellulases, hemicellulases, or mixtures thereof;
   f) reacting said higher solids biomass slurry under suitable conditions; and
   g) optionally repeating one or more steps (c), (d), (e), and (f) one or more times, whereby a high sugar content hydrolysate is produced, wherein the concentration of total soluble sugars produced is at least about 100 g/L, and wherein the yield stress of the slurry is maintained at less than 30 Pa.

2. The process of claim 1, wherein the mixable portion of a pretreated biomass slurry of step (a) (i) is provided by combining a heel of low viscosity component and a portion of pretreated biomass in the vertical stirred tank reactor and adjusting the temperature and pH prior to adding enzyme.

3. The process of claim 1 wherein the portions of biomass are added continuously.

4. The process of claim 1 wherein the dry weight of biomass in all pretreated biomass portions combined is greater than 20% of the weight of the final hydrolysate product.

5. The process of claim 1 wherein applying the particle size reduction mechanism is performed one or more times before, during, or after step (b), or any combination thereof.

6. The process of claim 1 wherein said size reduction mechanism comprises mechanical size reduction.

7. The process of claim 6 wherein said mechanical size reduction mechanism is immersed in the reactor tank or incorporated in a recycle loop.

8. The process of claim 1 wherein pH and temperature are controlled following adding an additional portion of pretreated biomass.

9. The process of claim 2 or 8 wherein the pH is adjusted to between about 4 and about 10.

10. The process of claim 9 wherein the pH is adjusted to be between about 4.5 and about 6.

11. The process of claim 2 or 8 where the temperature is adjusted to between about 20° C. and about 80° C.

12. The process of claim 11 wherein the temperature is adjusted to be between about 25° C. and about 60° C.

13. The process of claim 4 wherein the dry weight of biomass is at least about 24%.

14. The process of claim 13 wherein the dry weight of biomass is at least about 30%.

15. The process of claim 1 wherein one enzyme capable of hydrolyzing cellulose is selected from the group consisting of cellulases, endoglucanases, exoglucanases, cellobiohydrolases, -glucosidases.

16. The process of claim 1 wherein the first saccharification enzyme consortium of (a) (ii), the additional saccharification enzyme consortium of (e), and additional saccharification enzyme consortia of other optional repetitions may be comprised of the same or different enzymes.

17. The saccharification enzyme consortia of claim 16 wherein each consortium comprises cellulases, hemicellulases, or mixtures thereof.

18. The process of claim 1 wherein said biomass is selected from the group consisting of switchgrass, waste paper, sludge from paper manufacture, corn grain, corn cobs, corn husks, corn stover, corn fiber, grasses, wheat, wheat straw, hay, barley, barley straw, rice straw, sugar cane bagasse, sorghum, soy, components obtained from milling of grains, trees, branches, roots, leaves, wood chips, sawdust, shrubs and bushes, vegetables, fruits, flowers and animal manure.

19. The process of claim 18 wherein biomass is selected from the group consisting of corn cobs, corn stover, corn fiber, corn husks, sugar cane bagasse, sawdust, switchgrass, wheat straw, hay, rice straw, and grasses.

20. The process of claim 18 wherein biomass is selected from the group consisting of corn cobs, corn stover, corn fiber, sawdust, and sugar cane bagasse.

21. The process of claim 1 wherein said biomass is derived from multiple feedstocks.

22. The process of claim 1 wherein said high sugar content hydrolysate comprises monosaccharides and oligosaccharides.

23. The process of claim 22, wherein the concentration of sugars in said hydrolysate is at least about 100 g/L.

24. The hydrolysate produced by the process of claim 1.

* * * * *